US010171935B1

(12) United States Patent
Reyes et al.

(10) Patent No.: US 10,171,935 B1
(45) Date of Patent: Jan. 1, 2019

(54) HEALTHCARE PROXIMITY SERVICES

(71) Applicant: MicroStrategy Incorporated, Vienna, VA (US)

(72) Inventors: Benjamin Reyes, Great Falls, VA (US); Hugh Owen, Vienna, VA (US); Jose Nocedal de la Garza, Vienna, VA (US)

(73) Assignee: MicroStrategy Incorporated, Vienna, VA (US)

( * ) Notice: Subject to any disclaimer, the term of this patent is extended or adjusted under 35 U.S.C. 154(b) by 0 days.

(21) Appl. No.: 14/793,478

(22) Filed: Jul. 7, 2015

Related U.S. Application Data

(60) Provisional application No. 62/021,583, filed on Jul. 7, 2014.

(51) Int. Cl.
*H04W 4/021* (2018.01)
*G01S 1/68* (2006.01)
*H04W 88/02* (2009.01)
*G06Q 50/22* (2018.01)
*G06F 19/00* (2018.01)
*G16H 10/60* (2018.01)

(52) U.S. Cl.
CPC .............. *H04W 4/021* (2013.01); *G01S 1/68* (2013.01); *G06F 19/322* (2013.01); *G06Q 50/22* (2013.01); *G16H 10/60* (2018.01); *H04W 88/02* (2013.01)

(58) Field of Classification Search
CPC ...... H04W 64/00; H04W 4/02; H04W 72/048
See application file for complete search history.

(56) References Cited

U.S. PATENT DOCUMENTS

| 6,774,765 | B1 | 8/2004 | Goodwin, III | |
| 7,039,628 | B2* | 5/2006 | Logan, Jr. | G06F 19/322 |
| 7,319,386 | B2* | 1/2008 | Collins, Jr. | A61B 5/1115 |
| | | | | 340/286.07 |
| 8,781,502 | B1 | 7/2014 | Middleton | |

(Continued)

OTHER PUBLICATIONS

Notice of Allowance issued in U.S. Appl. No. 14/793,489 dated Apr. 29, 2016, 8 pages.

(Continued)

*Primary Examiner* — Vladimir Magloire
*Assistant Examiner* — Donald H Braswell
(74) *Attorney, Agent, or Firm* — Fish & Richardson P.C.

(57) ABSTRACT

Method, systems, and computer-readable media for receiving, from an application instance operating on a client device, healthcare information that indicates a client device identifier, a wireless proximity beacon identifier, and a proximity of the identified client device to the identified wireless proximity beacon. From the received healthcare information, a determination is made whether the proximity of the identified client device to the identified wireless proximity beacon satisfies a threshold proximity. Based at least on the determination, an action is determined that the application instance operating on the identified client device is permitted to perform while the proximity of the identified client device to the identified wireless proximity beacon satisfies the threshold proximity. Healthcare information is transmitted to the identified client device that enables the application instance operating on the identified client device to perform the action.

22 Claims, 12 Drawing Sheets

(56) References Cited

U.S. PATENT DOCUMENTS

| | | | | |
|---|---|---|---|---|
| 8,799,009 B2* | 8/2014 | Mellin | ................... | G06Q 10/06 703/10 |
| 2006/0049936 A1* | 3/2006 | Collins, Jr. | ........... | A61B 5/1115 340/539.11 |
| 2012/0323691 A1 | 12/2012 | Mclaughlin | | |
| 2013/0267253 A1 | 10/2013 | Case | | |
| 2014/0002236 A1 | 1/2014 | Pineau | | |
| 2014/0113560 A1* | 4/2014 | Graube | ................... | H04B 7/26 455/41.2 |
| 2014/0244819 A1 | 8/2014 | Patrick | | |
| 2014/0335893 A1* | 11/2014 | Ronen | ................... | G01S 5/0252 455/456.1 |
| 2015/0181383 A1 | 6/2015 | Schulz | | |
| 2015/0351008 A1 | 12/2015 | Mayor | | |

OTHER PUBLICATIONS

Notice of Allowance issued in U.S. Appl. No. 15/250,396 dated Jun. 15, 2017, 5 pages.
Office Action issued in U.S. Appl. No. 14/793,163 dated Jun. 27, 2016, 39 pages.
Office Action issued in U.S. Appl. No. 14/793,163 dated Mar. 23, 2017, 47 pages.
Office Action issued in U.S. Appl. No. 14/793,345 dated Aug. 10, 2016, 41 pages.
Office Action issued in U.S. Appl. No. 14/793,489 dated Jan. 11, 2016, 10 pages.
Office Action issued in U.S. Appl. No. 15/250,396 dated Oct. 20, 2016, 12 pages.

\* cited by examiner

HEALTHCARE PROXIMITY SERVICES

CROSS-REFERENCE TO RELATED APPLICATIONS

This application claims priority from U.S. Provisional Application No. 62/021,583, filed Jul. 7, 2014, and titled "Healthcare Proximity Services," which is incorporated by reference.

TECHNICAL FIELD

This disclosure relates generally to providing location-based information or services.

BACKGROUND

The physical locations of mobile devices can be determined using various techniques. Information or other services can be provided to users of client devices based on the physical location of the user's client device.

DETAILED DESCRIPTION

Figure 1:
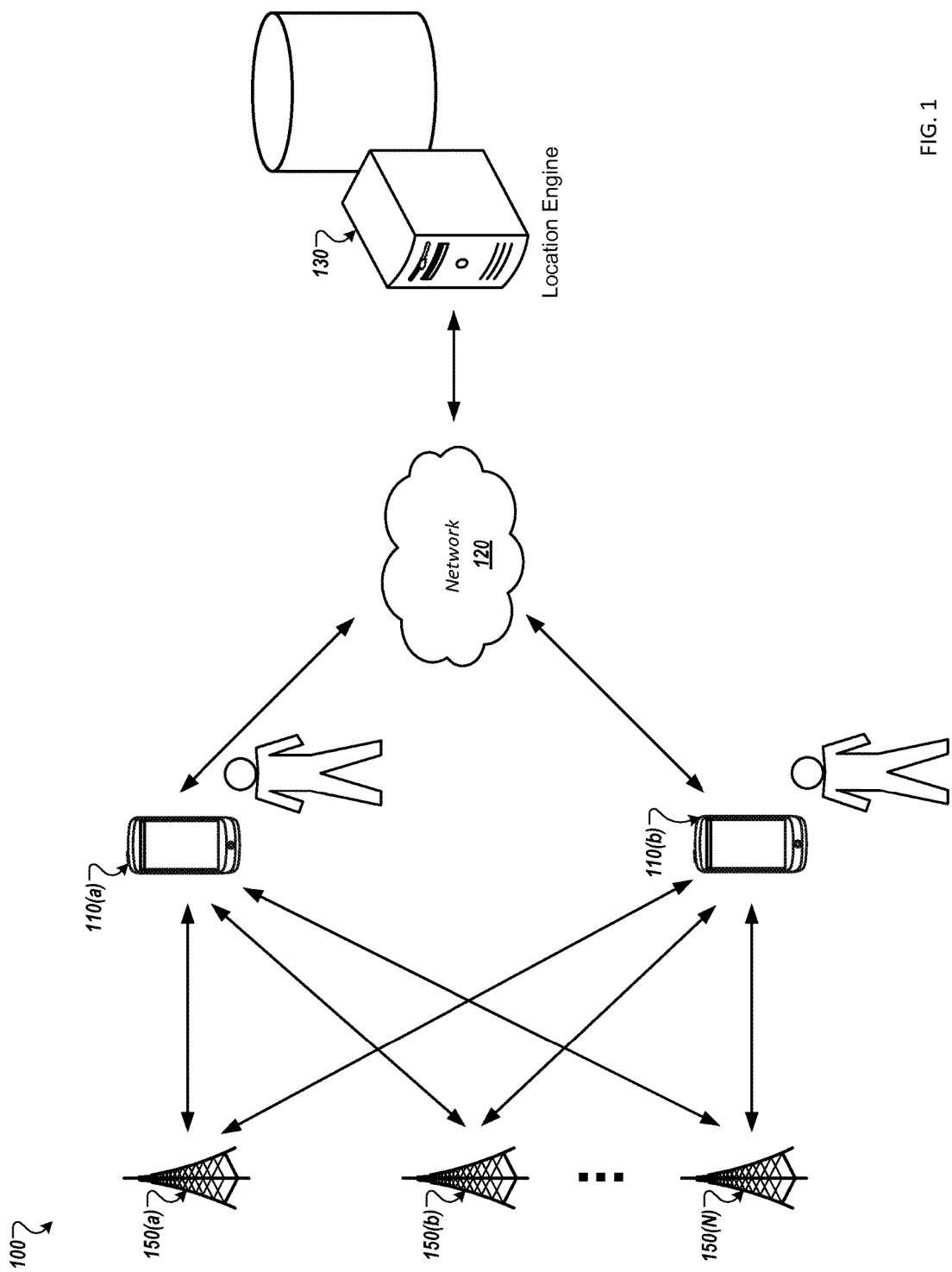
FIG. 1 illustrates an example system for providing proximity services using proximity detection technology.

Techniques are described for providing location-based services by utilizing proximity detection technology. A proximity detection system that includes one or more wireless sensor beacons can determine a client device's location based on the client device's proximity to one or more of the beacons. Based on the location of a particular client device, information can be provided to the client device, or other functionalities can be made accessible to the client device. Additionally, the locations of one or more client devices can be tracked and/or reported to one or more external systems, e.g., servers, such that the location information can be analyzed to determine various location statistics. For example, the proximity detection system can track the locations and/or movements of one or more client devices over time. The location statistics can further be combined with other information, such as user profile information associated with users of the one or more client devices, such that information in addition to the location information may be provided to users of the one or more client devices.

In some implementations, a proximity detection system is associated with a particular region, such as a building, venue, outdoor area, or other space, and includes one or more wireless sensor beacons. Each of the wireless sensor beacons is capable of emitting information identifying a particular beacon. A client device associated with a user can include software that is capable of detecting the presence of the wireless sensor beacons. Based on detecting the presence of one or more wireless sensor beacons, the client device can determine the client device's proximity to the one or more beacons. This proximity information can then be used to estimate the location of the user's client device relative to the one or more beacons.

In some implementations, each of the wireless sensor beacons is associated with a particular geographical location (e.g., latitude and longitude coordinates). As a result, determining the proximity of the client device to the one or more beacons enables for an estimation of a physical location of the client device. For example, the proximity detection system can estimate the location of a client device based on the client device's proximity to a particular beacon, or can be estimated using a trilateration or other multilateration process in which the client device's location is estimated based on the client device's proximity to three particular beacons. Other methods for estimating the location of a client device based on the proximity to one or more beacons are also possible.

Location information and/or other information (e.g., information associated with a user of a client device) can be exchanged between a client device and one or more servers that are accessible over a network. Location information can be tracked, for example, by storing a history of client device locations on a server, and statistical information can be determined regarding the locations and/or movements of one or more client devices. Information from the one or more servers can also be provided to one or more of the client devices over a network. Information provided to the client devices may be based at least in part on a location of the client device, or may be information provided based on detecting other events. In practice, other operations can be performed using a proximity detection system to locate one or more client devices. For example, various implementations can involve the use of a proximity detection system to provide location-based services in a hospital, medical office, or other space associated with providing healthcare services.

FIG. 1 illustrates an example of a proximity detection system 100 configured to provide location-based services by utilizing proximity detection technology. The proximity detection system 100 includes one or more client devices 110(a)-(b), a network 120, a location engine 130, and one or more wireless sensor beacons 150(a)-(N). The network 120 enables communication between the one or more client devices 110(a)-(b) and the location engine 130. The one or more client devices 110(a)-(b) are capable of communicating with the one or more wireless sensor beacons 150(a)-(N) using techniques described herein.

The wireless sensor beacons 150(a)-(N) can be devices capable of emitting and/or receiving information over a wireless communication channel. For example, the wireless sensor beacons 150(a)-(N) can utilize Bluetooth Low Energy (BLE), also known as Bluetooth Smart, or other wireless technologies, e.g., Wi-Fi, near-field communications (NFC), or other wireless technologies, to communicate with the client devices 110(a)-(b). The wireless sensor beacons 110(a)-(N) may be commercially available beacon devices, for example, iBeacon devices as made available by Apple Inc., Gimbal Proximity Beacons as made available by Qualcomm Incorporated, PayPal Beacon devices as made available by PayPal, or other devices. The wireless sensor beacons 150(a)-(N) can communicate with client devices 110(a)-(b) by emitting messages (e.g., pings) that include information identifying the beacons 150(a)-(N). In some implementations, client devices 110(a)-(b) can communicate with the wireless sensor beacons 150(a)-(N) by receiving messages from the wireless sensor beacons 150(a)-(N) that identify one or more of the wireless sensor beacons 150(a)-(N).

In some implementations, for example, each of the wireless sensor beacons 150(a)-150(N) is associated with identification information that identifies a particular wireless sensor beacon or group of two or more wireless sensor beacons. In some instances, a particular wireless sensor beacon may be associated with multiple identifiers that identify one or more groups of wireless sensor beacons that each includes the particular wireless sensor beacon, and/or an identifier that identifies the particular wireless sensor beacon within the one or more groups of wireless sensor beacons. In some implementations, the beacons 150(a)-(N) may all be associated with the same unique universal identifier (UUID). As an example, each of the beacons 150(a)-(N) may be associated with a particular building, and may therefore all be associated with the same UUID to indicate that all of the wireless sensor beacons 150(a)-(N) are associated with the same building. Additionally, a subset of wireless sensor beacons, for example, the wireless sensor beacons 150(a) and 150(b), may be associated with a second identifier that may be termed a major identifier. This identifier may identify a smaller subset of the wireless sensor beacons 150(a)-(N), for example, to indicate that all of the wireless sensor beacons 150(a)-(N) sharing the same UUID are associated with the same building, and that the wireless sensor beacons 150(a) and 150(b) are on the same floor of the building. Another identifier, termed a minor identifier, may identify a particular wireless sensor beacon within the one or more groupings of wireless sensor beacons. For example, the wireless sensor beacons 150(a) and 150(b) that have the same UUID and major identifier may have unique minor identifiers to distinguish the wireless sensor beacon 150(a) from the wireless sensor beacon 150(b). In some implementations, the UUID, major identifier, minor identifier, or other identifiers associated with one or more wireless sensor beacons may be alphanumeric identifiers, or may include other information or data, e.g., a data packet that is unique to a particular wireless sensor beacon or group of wireless sensor beacons.

The identifiers used to identify wireless sensor beacons may be associated with geographical locations or other defined regions. For example, an identifier may be associated with a particular set of latitude and longitude coordinates, may be associated with a defined region (e.g., a particular building, room of a building, venue, outdoor area, or other space), or may be defined in another way, for example, based on a function of the defined region (e.g., an office space versus a dining area). The wireless sensor beacons 150(a)-(N) of FIG. 1, for example, may each be associated with a UUID, a major identifier, and a minor identifier. The UUID may be shared by all of the beacons 150(a)-(N) and may be associated with a region corresponding to a particular building (e.g., a set of latitude and longitude coordinates that define the area covered by the building). A major identifier may be shared by a subset of wireless sensor beacons, such as the wireless sensor beacons 150(a) and 150(b), and be associated with another location, for example, a set of latitude and longitude coordinates for a particular department within the particular building. The minor identifier of each of the wireless sensor beacons 150(a)-150(N) may be unique to each wireless sensor beacon, and may be associated with a particular geographical location that defines the precise location of a wireless sensor beacon. For example, each wireless sensor beacon 150(a)-(N) would have a unique minor identifier that each are associated with a different geographical location. In some implementations, only one or a subset of the identifiers may be associated with a physical location. For example, each of the minor identifiers that identify individual wireless sensor beacons may be associated with a physical location (e.g., latitude and longitude), while a UUID or major identifier that is shared by multiple wireless sensor beacons may not.

Each of the wireless sensor beacons 150(a)-(N) can broadcast information to allow client devices 110(a)-(b) to recognize one or more of the wireless sensor beacons 150(a)-(N). In some instances, wireless sensor beacons broadcast their information periodically, for example, every second, every 100 milliseconds, every minute, etc. The wireless sensor beacons 150(a)-(N) can broadcast this information using the wireless communications protocol that the wireless sensor beacon is configured to use (e.g., Bluetooth Low Energy). In some implementations, the information broadcast by a wireless sensor beacon can be broadcast with a particular broadcast frequency or power level. The information broadcast by a wireless sensor beacon can have a predefined format. For example, the information broadcast by each of the wireless sensor beacons 150(a)-(N) may utilize the same format that includes the wireless sensor beacons' UUID, major identifier, and/or minor identifier (e.g., in a particular order or using a particular hashing method). Information broadcast by the wireless sensor beacons may take other forms as well, for example, pings or other information. The information periodically broadcast by the wireless sensor beacons 150(a)-(N) can be received by the client devices 110(a)-(b) such that the client devices 110(a)-(b) can detect the presence of and/or the identity of one or more of the wireless sensor beacons 150(a)-(N).

The one or more client devices 110(a)-(b) are devices that host one or more applications, for example, one or more applications associated with providing location-based services using proximity detection technology. The one or more client devices 110(a)-(b) can be cellular devices or non-cellular locally networked devices. The client devices 110(a)-(b) can include a cell phone, a smart phone, a tablet PC, a personal digital assistant ("PDA"), or any other stationary or portable device configured to communicate with the mobile sensor beacons 150(a)-(N) and to communicate over a network, such as the network 120. For example, implementations can include iPhone-type devices, e.g., as provided by Apple Inc., BlackBerry-type devices, e.g., as provided by BlackBerry Ltd., iPod or iPad-type devices, e.g., as provided by Apple Inc., other portable music or media players, or other communication devices including other handled, portable, or stationary devices for gaming, communications, and/or data organization. The client devices 110(a)-(b) can be the same, or can be devices of different types. The one or more client devices 110(a)-(b) can perform functions unrelated to the proximity detection system 100, such as placing personal telephone calls, playing music, playing video, displaying pictures, browsing the Internet, maintaining an electronic calendar, modifying or organizing data, etc.

The client devices 110(a)-(b) can further be equipped to detect the presence of and/or receive information from the wireless sensor beacons 150(a)-(N). For example, the wireless sensor beacons 150(a)-(N) may be Bluetooth Low Energy devices, and the client devices 110(a)-(b) may be capable of detecting signals broadcast by, or receiving the information broadcast by, the wireless sensor beacons 150(a)-(N).

Upon detecting and/or receiving signals from one or more wireless sensor beacons 150(a)-(N), a client device 110(a)-(b) can perform additional operations to provide location-based services using proximity detection technology. For example, the client device 110(a) can receive information broadcast by the wireless sensor beacon 150(a). The client device 110(a) can use this information to identify the wireless sensor beacon 150(a), and can use the strength of the signal received from the wireless sensor beacon 150(a) to estimate the client device's 110(a) proximity to the wireless sensor beacon 150(a). Based on identifying the wireless sensor beacon 150(a) and the proximity of the client device 110(a) to the wireless sensor beacon 150(a), a location of the client devices 110(a) may be estimated. In some implementations, identifying the wireless sensor beacon 150(a) and/or estimating the physical location of the client device 110(a) based on the information broadcast by the wireless sensor beacon 150(a) can be performed by an application hosted by the client device 110(a). In other implementations, the client device 110(a) can exchange communications with another system, such as the location engine 130, to identify the wireless sensor beacon 150(a) and/or to estimate the physical location of the client device 110(a).

Each of the client devices 110(a)-(b) having an application instance for providing location-based services using the proximity detection system may be associated with an identifier that uniquely, and in some implementations anonymously, identifies each of the client devices 110(a)-(b). For example, when the application is installed on a particular client device, the proximity detection system may assign the particular client device, the application instance installed on the client device, or a user of the client device a unique identifier. The location proximity detection system can log information, such as location history information, for the client device using the unique identifier, such that the logged information is essentially anonymous. In other implementations, an identifier assigned by the proximity detection system may be linked to a particular user, a particular client device, a particular user profile (e.g., a social network profile), etc.

In some implementations, in order to reduce power consumption of the client devices 110(a)-110(b) while running the location-based services application, the client devices 110(a)-110(b) are operated in several different modes. For example, a client device can operate in a low-power, region monitoring mode until one or more of the wireless sensor beacons 150(a)-(N) are detected, and can then enter a ranging mode to identify one or more of the wireless sensor beacons 150(a)-(N) for the purposes of estimating a physical location of the client device.

For example, a client device 110(a) having an application for location-based services that utilize proximity detection technology can operate in a low-power, region monitoring mode. This mode may be active at all times that the client device 110(a) is active or powered on, may be active while the application is actively running (e.g., in the "foreground"), or while the application is running but is not active (e.g., in the "background"). In some implementations, while operating in the region monitoring mode, the client device 110(a) can detect the presence of one or more wireless sensor beacons 150(a)-(N). For example, the client device 110(a) may detect the presence of a wireless sensor beacon 150(a)-(N) based on detecting a ping broadcast by a wireless sensor beacon 150(a)-(N), or based on detecting other information transmitted by the wireless sensor beacon 150(a)-(N), e.g., the wireless sensor beacon's 150(a)-(N) identifying information. The client device 110(a) may detect only the presence of the one or more wireless sensor beacons 150(a)-(N) such that the client device 110(a) does not identify a particular wireless sensor beacon 150(a)-(N) or group of wireless sensor beacons 150(a)-(N), but rather only that a wireless sensor beacon is within range. In other implementations, detection of the presence of one or more wireless sensor beacons 150(a)-(N) by the client device 110(a) can involve identifying a group of, or an individual, wireless sensor beacons 150(a)-(N). For example, the client device 110(a) can detect the presence of one or more wireless sensor beacons 150(a)-(N) while in region monitoring mode based on receiving information identifying a group of the wireless sensor beacons 150(a)-(N), such as a UUID or major identifier shared by a subset of the wireless sensor beacons 150(a)-150(N), or based on receiving information identifying a particular wireless sensor beacon 150(a)-(N), such as a particular minor identifier.

In some implementations, a client device can be configured to detect the presence of certain wireless sensor beacons while operating in region monitoring mode. For example, a client device 110(a)-110(b) can be configured to detect the presence of one or more wireless sensor beacons 150(a)-(N) that share the same identifier or that have a particular identifier, such as a particular UUID, major identifier, or minor identifier. As an example, the client device 110(a) may only be configured to detect the presence of wireless sensor beacons 150(a)-(N) that are associated with a particular UUID corresponding to a particular building. In other examples, the client device 110(a) may only be configured to detect the presence of wireless sensor beacons 150(a)-(N) that are associated with a particular region of a building and that are associated with a major identifier associated with that region of the building, or may be configured to only detect the presence of a particular wireless sensor beacon 150(a)-(N) that is associated with a particular minor identifier. Using these techniques, the client device 110(a)-(b) may remain in a low-power state for as much time as possible, only becoming active (i.e., ranging) when necessary. For example, using the region monitoring mode, the client device 110(a) may avoid ranging unless the client device 110(a) is in a region relevant to a user of the client device 110(a), or unless the client device 110(a) is in a location where the location-based services provided by the proximity detection system are available.

Based on detecting the presence of one or more wireless sensor beacons, a client device can transition from the low-power, region monitoring mode to a ranging mode. While in ranging mode, the client device can identify one or more wireless sensor beacons and can additionally obtain other information relevant to providing location-based services, such as by estimating the proximity of the client device to one or more of the identified wireless sensor beacons. For example, the client device 110(a) operating in region monitoring mode may detect the presence of the wireless sensor beacon 150(a) based on receiving data broadcast by the wireless sensor beacon 150(a) that includes a particular UUID associated with the wireless sensor beacon 150(a). In response, the client device 110(a) may enter ranging mode, and may identify one or more wireless sensor beacons 150(a)-(N). Identifying one or more wireless sensor beacons 150(a)-(N) while in ranging mode may involve receiving information identifying each, or a subset of, the wireless sensor beacons 150(a)-(N), for example, the UUID, major identifier, and/or minor identifier of the wireless sensor beacons 150(a)-(N). Additionally, the client device 110(a) may determine the signal strength of the signals received from one or more of the wireless sensor beacons 150(a)-(N). For example, the client device 110(a) may measure the absolute signal strength of the received signals (e.g., in Watts), or may measure the signal strength in other ways (e.g., as a ratio measured in decibel-Watts). In some implementations, each of the wireless sensor beacons 150(a)-(N) may emit signals at a predetermined or known power level, such that a proximity to a particular wireless sensor beacon may be estimated based on the difference between the transmitted signal power and the signal power received at a client device.

While, in most applications, the data transferred between the client devices 110(a)-(b) and the wireless sensor beacons 150(a)-(N) is limited to the exchange of wireless sensor beacon identifier information, in some implementations, other information may be exchanged between the client devices 110(a)-(b) and the wireless sensor beacons 150(a)-(N). For example, information exchanged may include information relating to the battery level of one or more of the wireless sensor beacons 150(a)-(N), error messages, preferences or settings, identifier information, information identifying a client device 110(a)-(b), information identifying a user or user profile associated with one or more client devices 110(a)-(b), or other information.

Based on identifying one or more wireless sensor beacons 150(a)-(N) and, in some implementations, obtaining data used to estimate the proximity to one or more of the wireless sensor beacons 150(a)-(N) (e.g., data indicating the strength of the received signals), the client device 110(a) can perform operations to estimate a location of the client device 110(a) or can determine other operations to perform. For example, the client device 110(a) can estimate its location based on receiving information identifying one or more wireless sensor beacons 150(a)-(N) and based on obtaining information used to determine the proximity of the client device 110(a) to the one or more wireless sensor beacons 150(a)-(N). The client device 110(a) can estimate this location based on accessing information defining a geographical location or region associated with one or more of the identified wireless sensor beacons 150(a)-(N) and the information used to determine the proximity to one or more of the wireless sensor beacons 150(a)-(N). This process is described in greater detail with respect to FIG. 2.

The client device 110(a) may determine other operations to perform based on receiving the information identifying one or more wireless sensor beacons 150(a)-(N) or a proximity to one or more of the wireless sensor beacons 150(a)-(N). For example, based on identifying one or more wireless sensor beacons 150(a)-(N) associated with a particular identifier, or based on determining a proximity to one or more particular wireless sensor beacons 150(a)-(N), the client device 110(a)-(b) can access particular information or content. For example, the client device 110(a)-(b) can determine information to provide to a user of the client device 110(a)-(b) based on the user's client device 110(a)-(b) being located near one or more particular wireless sensor beacons 150(a)-(N) or within a threshold proximity of one or more wireless sensor beacons 150(a)-(N). Other information may be accessed or other operations may be performed based on the received wireless sensor beacon information and/or information indicating the proximity to particular wireless sensor beacons. In some implementations, data accessed by a client device may be accessed locally at the client device, or operations performed by a client device may be performed locally at the client device. In other implementations, the client device may access information at a remote location, for example, at the location engine 130, or may cause operations to be performed at a location remote from the client device, for example, at the location engine 130.

When information is accessed or performed remotely from a particular client device 110(a)-(b), information may be exchanged between the client device and the location engine 130 using one or more networks 120. For example, a client device 110(a) can transmit data to the location engine 130 over the network 120 identifying one or more wireless sensor beacons 150(a)-(N) and/or the proximity of the client device 110(a) to one or more of the wireless sensor beacons 150(a)-(N). The location server 130 can receive the information from the client device 110(a), and in response can perform operations on the received information or provide information to the client device 110(a) over the network 120.

The network 120 is configured to enable electronic communications between devices connected to the network 120. For example, the network 120 can be configured to enable the exchange of electronic communications between the client devices 110(a)-(b) and the location engine 130.

The network 120 can include, for example, one or more of the Internet, Wide Area Networks (WANs), Local Area Networks (LANs), e.g., Wi-Fi, analog or digital wired and wireless telephone networks, e.g., a public switched telephone network (PSTN), Integrated Services Digital Network (ISDN), a cellular network, and Digital Subscriber Line (DSL), Ethernet, Internet Protocol (IP) over broadband, radio, television, cable, satellite, or any other delivery or tunneling mechanism for carrying data. Network 120 can include multiple networks or subnetworks, each of which can include, for example, a wired or wireless data pathway. The network 120 can include a circuit-switched network, a packet-switched data network, or any other delivery or tunneling mechanism for carrying data (e.g., data or voice communications). For example, the network 120 can include networks based on the Internet protocol (IP), asynchronous transfer mode (ATM), the PSTN, packet-switched networks based on IP, X.25, or Frame Relay, or other comparable technologies and can support voice using, for example, VoIP, or other comparable protocols used for voice communications. The network 120 can include one or more networks that include wireless data channels and wireless voice channels. The network 120 can be a wireless network, a broadband network, or a combination of networks including a wireless network and a broadband network. In some implementations, the network 120 can include one or more individual networks.

The location engine 130 can include one or more servers and can communicate with the client devices 110(a)-(b) over the network 120. In some implementations, the location engine 130 can be able to access and store information, for example, information received from the client devices 110(a)-(b). Such information may include, for instance, information identifying the one or more client devices 110(a)-(b) (e.g., an identifier for the client devices 110(a)-(b)), estimated locations of the client devices 110(a)-(b), information identifying one or more wireless sensor beacons 150(a)-(N), information relating to the proximity of one or more wireless sensor beacons 150(a)-(N) to one or more client devices 110(a)-(b), information associated with user or device profiles associated with the client devices 110(a)-(b), etc. In some instances, the location engine 130 can access other information that is available at one or more other servers that are in communication with the location engine 130, or information that is otherwise accessible, e.g., over the network 120. Such information may include information or content to provide to the client devices 110(a)-(b), or can include other information. In some implementations, the location engine 130 can receive information from one or more sources and can perform analysis on the received information. For example, the location engine 130 may be able to identify particular content to provide to the client device 110(a) based on receiving information indicating, or otherwise determining, a location of the client device 110(a).

In some implementations, the location engine 130 can also store information relevant to location-based services provided by the proximity detection system. For example, the location engine 130 may receive information from the client device 110(a) that identifies one or more particular wireless sensor beacons 150(a)-(N) and a proximity of the client device 110(a) to the particular wireless sensor beacons 150(a)-(N), and can estimate the physical location (e.g., latitude and longitude) of the client device 110(a) at the particular time when the data was received and/or obtained by the client device 110(a). The location engine 130 can store information tracking the location of the client device 110(a) and/or other client devices 110(a)-(b) over time and can perform additional analysis on the location data, where the results of such analysis may also be stored by the location engine 130.

Figure 2:
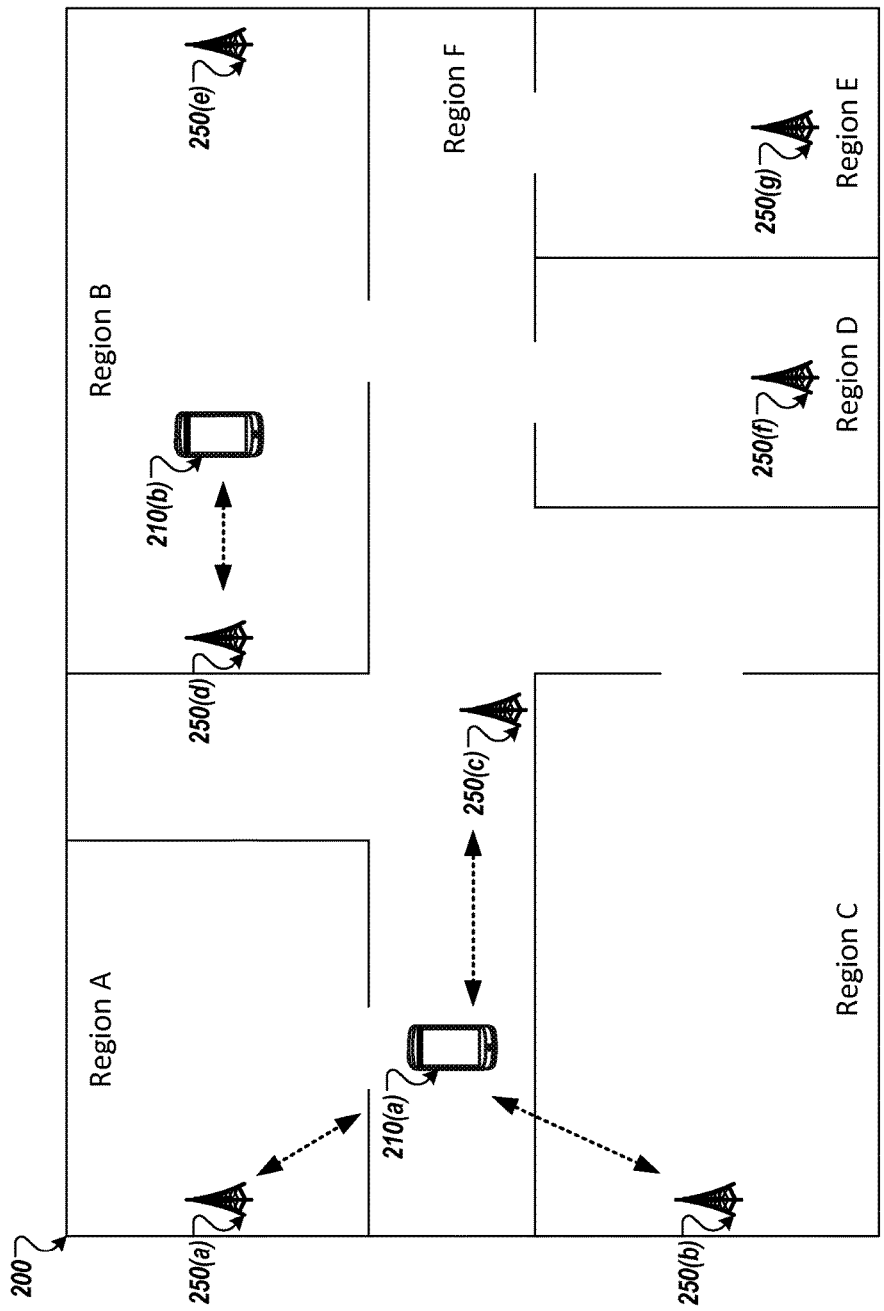
FIG. 2 depicts an example system for using proximity detection technology to determine a physical client device location.

FIG. 2 illustrates an example implementation in which the proximity detection system of FIG. 1 is used to estimate the location of one or more client devices. As shown in FIG. 2, a space 200 can be divided into several regions. For instance, the space 200 is shown divided into regions A through F. The space 200 may be, for example, a building, a particular floor of a building, a venue (e.g., stadium, concert hall, festival, etc.), an outdoor area (e.g., a park, a city, etc.), or any other space. The space 200 can be associated with multiple wireless sensor beacons 250(a)-(g) that are positioned throughout the space 200. The multiple wireless sensor beacons 250(a)-(g) may be associated with identifier information that is shared across multiple wireless sensor beacons 250(a)-(g), such as a UUID or major identifier, and/or may be associated with identifier information that is unique to each of the wireless sensor beacons 250(a)-(g), such as unique minor identifiers.

Based on the space 200 being associated with the wireless sensor beacons 250(a)-(g), a location of the client devices 210(a)-(b) may be estimated. Each of the client devices 210(a)-(b) may host an application for providing location-based services using the proximity detection technology utilized by the proximity detection system. At a particular point in time, the client devices 210(a)-(b) may be running the application actively (in the "foreground"), in standby (in the "background"), or may not be running the application at all. The client devices 210(a)-(b) may further be operating in the low-power, region monitoring mode. While operating in this mode, the client devices 210(a)-(b) may detect the presence of one or more of the wireless sensor beacons 250(a)-(g). In some implementations, as described, the client devices 210(a)-(b) may detect the presence of any wireless sensor beacon regardless of it associated UUID, major identifier, or minor identifier. In other implementations, the client devices 210(a)-(b) may detect the presence only of particular wireless sensor beacons 250(a)-(g) that are associated with particular UUIDs, major identifiers, and/or minor identifiers. Based on detecting the presence of one or more wireless sensor beacons 250(a)-(g), the client devices 210(a)-(b) may enter ranging mode to identify one or more wireless sensor beacons 250(a)-(g) that are in range of the client devices 210(a)-(b).

While the client devices 210(a)-(b) are in ranging mode, information received and/or obtained by the client devices 210(a)-(b) can include information identifying particular wireless sensor beacons 250(a)-(g) (e.g., the UUID, major identifier, and minor identifier of each wireless sensor beacon 250(a)-(g) that is within range). The information received and/or obtained by a particular client device 210(a)-(b) may further include information indicating, or that can be used to determine, the proximity of the particular client device 210(a)-(b) to particular wireless sensor beacons 250(a)-(g). For example, a client device 210(a) can obtain information indicating a strength of signal received from a particular wireless sensor beacon 250(a), and can use the signal strength information to determine the proximity of the client device 210(a) to the particular wireless sensor beacon 250(a). Alternatively, the client device 210(a) can receive information indicating the proximity of the client device 210(a) to the particular wireless sensor beacon 250(a). In such an implementation, the client device 210(a) may receive information indicating its proximity to the wireless sensor beacon 250(a) based on providing the location engine 130 information indicating the strength of a signal received from the wireless sensor beacon 250(a), where the location engine 130 can calculate the proximity of the wireless sensor beacon 250(a) to the client device 210(a) and provide information to the client device 210(a) indicating the client device's 210(a) proximity to the wireless sensor beacon 250(a). In some implementations, the wireless sensor beacons 250(a)-(g) can be calibrated to ensure that the determined proximity to a particular wireless sensor beacon is accurate.

Based on the information identifying the wireless sensor beacons 250(a)-(g) and the proximity of the wireless sensor beacons 250(a)-(g) to a particular client device 210(a)-(b), the location of a particular client device 210(a)-(b) can be estimated. In some implementations, the location of a client device can be estimated based on determining the closest wireless sensor beacon to the client device. In other implementations, the location of a client device can be estimated by using trilateration or by other methods that can provide estimates of locations based on an object's proximity to one or more other objects.

As an example, the location of the client device 210(b) may be estimated based on determining the closest wireless sensor beacon 250(a)-250(g) to the client device 210(b). Upon detecting the presence of one or more wireless sensor beacons 250(a)-(g), that is, upon entering ranging mode, the client device 210(b) may identify and determine a proximity to one or more of the wireless sensor beacons 250(a)-(g). The client device 210(b) may then identify a particular wireless sensor beacon 250(d) to which it is the closest from among the wireless sensor beacons 250(a)-(g), for example, based on determining that the strength of the signal received from the wireless sensor beacon 250(d) is the strongest among the signals received by the wireless sensor beacons 250(a)-(g) that have been identified by the client device 210(b). The client device 210(b) may then estimate its proximity to the wireless sensor beacon 250(d) based on the received signal strength. In some implementations, estimating the location of the client device 210(b) can involve determining the proximity of the client device 210(b) to the wireless sensor beacon 250(d) multiple times (e.g., periodically), and using an average or running average of the multiple proximity measurements as the proximity of the client device 210(*b*) to the wireless sensor beacon 250(*d*). By averaging multiple proximity measurements, the proximity detection system can reduce the effects of interference or transient events that could influence the proximity measurements (e.g., a user opening or closing a door).

Based on determining the proximity of the client device 210(*b*) to the wireless sensor beacon 250(*d*), a geographical location or region associated with the closest wireless sensor beacon 250(*d*) can then be determined. For example, the client device 210(*b*) may store information that identifies the geographical location or region associated with each wireless sensor beacon 250(*a*)-(*g*), identified by their identifiers, and may access the information to determine the geographical location or region associated with the wireless sensor beacon 250(*d*). In other implementations, such information mapping the geographical locations or regions associated with the wireless sensor beacons 250(*a*)-(*g*) to the identifiers associated with those wireless sensor beacons 250(*a*)-(*g*) may be accessible by the client device 210(*b*) elsewhere, for example, at the location engine 130. Based on determining the most proximate wireless sensor beacon 250(*d*), the client device 210(*b*) (or alternatively the location engine 130) can estimate the location of the client device 210(*b*). For instance, the estimated location of the client device 210(*b*) may be a location that corresponds to the determined proximity from the wireless sensor beacon 250(*d*) in which the client device 210(*b*) could conceivably be located (e.g., not within a wall of a building). The client device 210(*b*) and/or the location engine 130 may then document the estimated location of the client device 210(*b*) at that particular point in time. For example, the client device 210(*b*) can locally store information logging the estimated location and the particular time, or can transmit information indicating the estimated location and the particular time to the location engine 130 for storage.

In another implementation, trilateration may be used to estimate the location of a client device, for example, the client device 210(*a*). Such a process enables the estimation of the absolute or relative location of the client device 210(*a*) based on the proximity of the client device 210(*a*) to three wireless sensor beacons of the wireless sensor beacons 250(*a*)-(*g*). In other implementations, a multilateration process may be used to estimate the location of a client device, where the multilateration process utilizes any number of two or more wireless sensor beacons to determine an approximate location of a client device. In some instances, the wireless sensor beacons selected to perform the trilateration or multilateration process can be those that are determined to be the closest to the client device 210(*a*), or the wireless sensor beacons selected to perform the trilateration process may be selected in a different way (e.g., the selected wireless sensor beacons may be preferred wireless sensor beacons). In some instances, selection of the wireless sensor beacons used to perform trilateration can be based on a previously estimated location of a client device. For example, based on determining that the client device 210(*a*) was previously located in region A of the space 200, the proximity detection system may select the wireless sensor beacons 250(*a*), 250(*b*), and 250(*c*) to perform trilateration. These wireless sensor beacons may be selected regardless of the detected signal strengths of the wireless sensor beacons. For example, even if the client device 210(*a*) determines that it received a stronger signal from the wireless sensor beacon 250(*d*) than it did from the wireless sensor beacon 250(*b*), the wireless sensor beacon 250(*b*) may be selected since it is closer to a previously estimated location of the client device 210(*a*). Additionally, in some instances, selection of the wireless sensor beacons used to perform the trilateration or other multilateration process is based on determining that certain geometries are preferable for determining the approximate location of a client device, for example, based on the detected angles between wireless sensor beacons and a client device.

In the example shown in FIG. 2 which uses a trilateration process to estimate a location of a client device, upon detecting the presence of one or more wireless sensor beacons 250(*a*)-(*g*), that is, upon entering ranging mode, the client device 210(*a*) may identify and determine a proximity to one or more of the wireless sensor beacons 250(*a*)-(*g*). The client device 210(*a*) may then select three of the identified wireless sensor beacons 250(*a*)-(*g*). For example, client device 210(*a*) may select the wireless sensor beacons 250(*a*), 250(*b*), and 250(*c*) that are determined to be the closest to the client device 210(*a*), based on detecting the proximity of the client device 210(*a*) to each of the wireless sensor beacons 250(*a*)-(*g*).

In other implementations, wireless sensor beacons 250(*a*)-(*g*) can be selected based on factors in addition to or in lieu of their proximity to the client device 210(*a*). For example, the proximity detection system may select a particular wireless sensor beacon based on the particular wireless sensor beacon being a preferred wireless sensor beacon or a wireless sensor beacon whose signal is not affected by obstacles or materials that the signal must travel through, e.g., walls. In some implementations, wireless sensor beacons may be selected based on the geometry formed by the wireless sensor beacons and a client device. For example, in performing trilateration, it is preferred that the angles formed by the wireless sensor beacons and the client device (e.g., with the client device forming the vertex of the angle) are acute angles or right angles. Thus, the selection of wireless sensor beacons may be based at least in part on determining wireless sensor beacons that form acute or right angles with the client device, such that wireless sensor beacons that form obtuse angles with the client device are not selected. In some implementations, the selection of wireless sensor beacons may consider multiple factors. For example, a particular wireless sensor beacon may be selected based on a combination of the detected signal strength of the wireless sensor beacon, the estimated proximity of the wireless sensor beacon to a client device, and the geometries (e.g., angles) formed between the particular wireless sensor beacon, the client device, and other wireless sensor beacons.

In some implementations, selecting wireless sensor beacons used to estimate the location of a client device may be dependent on determining that the signals received from one or more wireless sensor beacons satisfy a signal strength threshold. For example, a client device can determine the strength of the signals received from one or more wireless sensor beacons and can compare the detected signal strength to a signal strength threshold. If none of the detected signals meet the signal strength threshold, the proximity detection system may determine that a client device's location cannot be estimated, or may estimate the client device's location based on previous location estimates. For example, a location of a client device may be estimated based on a previous location estimate of the client device, an estimated speed and direction of movement of the client device, and/or historical movement data for the client device. If less than three of the identified wireless sensor beacons have detected signal strengths meeting the signal strength threshold, the proximity detection system may estimate the location of the client device based on the proximity of the client device to one (or both) of the wireless sensor beacons that have a received signal strength satisfying the threshold. This estimation may also be supplemented or adjusted based on previous estimates of the location of the client device, an estimated velocity or direction of movement for the client device, etc. If three or more of the identified wireless sensor beacons are determined to have received signal strengths satisfying the signal strength threshold, then wireless sensor beacons may be selected for estimation of the client device's location using trilateration. The selected wireless sensor beacons may be the wireless sensor beacons having the strongest received signal strength. In some implementations, the selection of wireless signal beacons to use in trilateration is dependent on the difference in the received signal strengths. For example, if the difference between the third strongest received signal and the fourth strongest or other received signal is above a certain threshold amount, then the three wireless sensor beacons with the strongest signals are selected for trilateration. If the difference in signal strength between the third strongest received signal and the fourth strongest or other received signal does not satisfy the threshold amount, then the wireless sensor beacons selected for trilateration may be a different set of wireless sensor beacons. For example, the wireless sensor beacons selected for trilateration can be selected from among the set of all wireless sensor beacons with received signal strengths that satisfy the signal strength threshold. The selection of the wireless sensor beacons may be determined based on geometric considerations (e.g., based on the angles formed between the wireless sensor beacons and the client device), based on a previously estimated location of the client device (e.g., based on determining which of the wireless sensor beacons are likely the closest to the client device), based on the relative signal strengths of the wireless sensor beacons, based on angles that would result in the trilateration calculation, or based on other factors. After selecting the wireless sensor beacons for trilateration, the proximity detection system can estimate the location of the client device using trilateration, and may also supplement and/or confirm the estimation of the client device's location with other information, for example, previously estimated locations, directions of movement, or rates of movement of the client device. In some implementations, the location estimate determined using any of the above methods may be further supplemented to confirm or adjust the location estimate, for example, by confirming that it is possible for the client device to be located in the estimated location.

Once the wireless sensor beacons 250(*a*), 250(*b*), and 250(*c*) have been selected and the identities and proximities of the selected wireless sensor beacons 250(*a*), 250(*b*), and 250(*c*) to the client device 210(*a*) have been determined, the location of the client device 210(*a*) may be estimated. For example, the geographical locations or regions associated with each of the wireless sensor beacons 250(*a*), 250(*b*), and 250(*c*) can be determined using techniques previously described, such as by accessing a lookup table mapping wireless sensor beacon identifier information to physical locations. A position of the client device 210(*a*) relative to the wireless sensor beacons 250(*a*), 250(*b*), and 250(*c*) can be estimated using trilateration. Based on the information indicating the physical locations or regions associated with the wireless sensor beacons 250(*a*), 250(*b*), and 250(*c*) and the position of the client device 210(*a*) relative to the wireless sensor beacons 250(*a*), 250(*b*), and 250(*c*), an estimate of the physical location of the client device 210(*a*) can be determined. The client device 210(*a*) and/or the location engine 130 may then document the estimated location of the client device 210(*a*) at that particular point in time.

In some implementations, estimating a physical location of a client device can utilize multiple estimates of the client device's physical location. For example, the proximity detection system may estimate the location of a client device by using both a multilateration process and by estimating the location based on the proximity of the client device to the nearest wireless sensor beacon to the client device. The proximity detection system may estimate the location of the client device based on the combination of these two estimates, for example, by averaging the two estimated locations. Determining the estimated location of a client device based on two or more estimates may consider other factors as well, for example, the estimated location of a client device may be based on averaging the multiple location estimates for the client device (e.g., taking the average of an estimated location determined by using a multilateration process and an estimated location determined using the closest wireless sensor beacon to the client device) and "snapping" that estimated location to a location where the client device could potentially be located. For example, if the average of two estimated locations for the client device is within a wall of a building, the proximity detection system can "snap" the location of the client device to a hallway next to the wall.

In some implementations, determining the proximity of a client device to a wireless sensor beacon can involve determining an estimated proximate distance of one to the other. For example, the client device 210(*a*) may determine that it is approximately 5 meters from the wireless sensor beacon 250(*a*). Such estimates may be dependent upon absorption of the signals broadcast by the wireless sensor beacons by other materials, such as the materials forming walls in a building. As a result of this phenomenon, it is possible that a wireless sensor beacon may be estimated as being further away from a client device than it actually is, since the signal received by the client device is weaker than it would typically be if not affected by its passing through other media, e.g., walls. In other implementations, determining the proximity of a client device to a wireless sensor beacon can involve classifying the client device as being immediate, e.g., from 0 to 3 meters, near, e.g., from 3 to 6 meters, or far, e.g., greater than 6 meters, from the wireless sensor beacon.

Additionally, as described, an application associated with a particular client device and/or the location engine 130 may maintain information that identifies locations within a space that a client device may be located. In such implementations, if an estimated location of a client device is determined to be a location in which the client device may not be located, the estimated location of the client device may be adjusted (e.g., "snapped") such that the estimated location is a permissible location. For example, the client device 210(*a*) and/or the location engine 130 may maintain a map of the space 200 of FIG. 2. If the estimated location of the client device 210(*a*) is determined to be within a wall of the space 200, such that the estimated location is not a possible location for the client device 210(*a*) to be located, the estimated location of the client device 210(*a*) may be "snapped to" or otherwise adjusted to a permissible location, e.g., the closest permissible location to the initially estimated location.

In some implementations, the wireless sensor beacons 250(*a*)-(*g*) may be reconfigurable, such that the proximity detection system can reconfigure the wireless sensor beacons 250(*a*)-(*g*) of the space 200. For example, if the proximity detection system determines that a particular wireless sensor beacon is not currently being used or is not used during specific hours of the day (e.g., that client devices do not identify the wireless sensor beacon during those hours), the proximity detection system may turn off the particular wireless sensor beacon or may turn off the wireless sensor beacon during the hours when the wireless sensor beacon is not used. In other examples, the proximity detection system may be able to monitor the accuracy and/or usefulness of a particular beacon. For example, if the proximity detection system determines that a particular wireless sensor beacon does not provide accurate location estimations, the proximity detection system can flag the wireless sensor beacon as needing to be moved or replaced. In other examples, the proximity detection system can determine that a particular wireless sensor beacon is largely redundant (e.g., is not necessary to providing accurate location estimates), and therefore may be better utilized by repositioning the wireless sensor beacon to a different area of a space, or that the wireless sensor beacon can be removed from the space. Reconfiguring the wireless sensor beacons within a space may allow for more accurate location estimating and/or more efficient use of resources including power usage and the deployment of available wireless sensor beacons.

Based on determining and tracking the estimated locations of one or more client devices within a particular space, various information can be determined about the space, the presence and distribution of users within the space, the movement of users throughout the space, and other spatial and/or temporal factors relating to the use of the space by one or more users.

Figure 3:
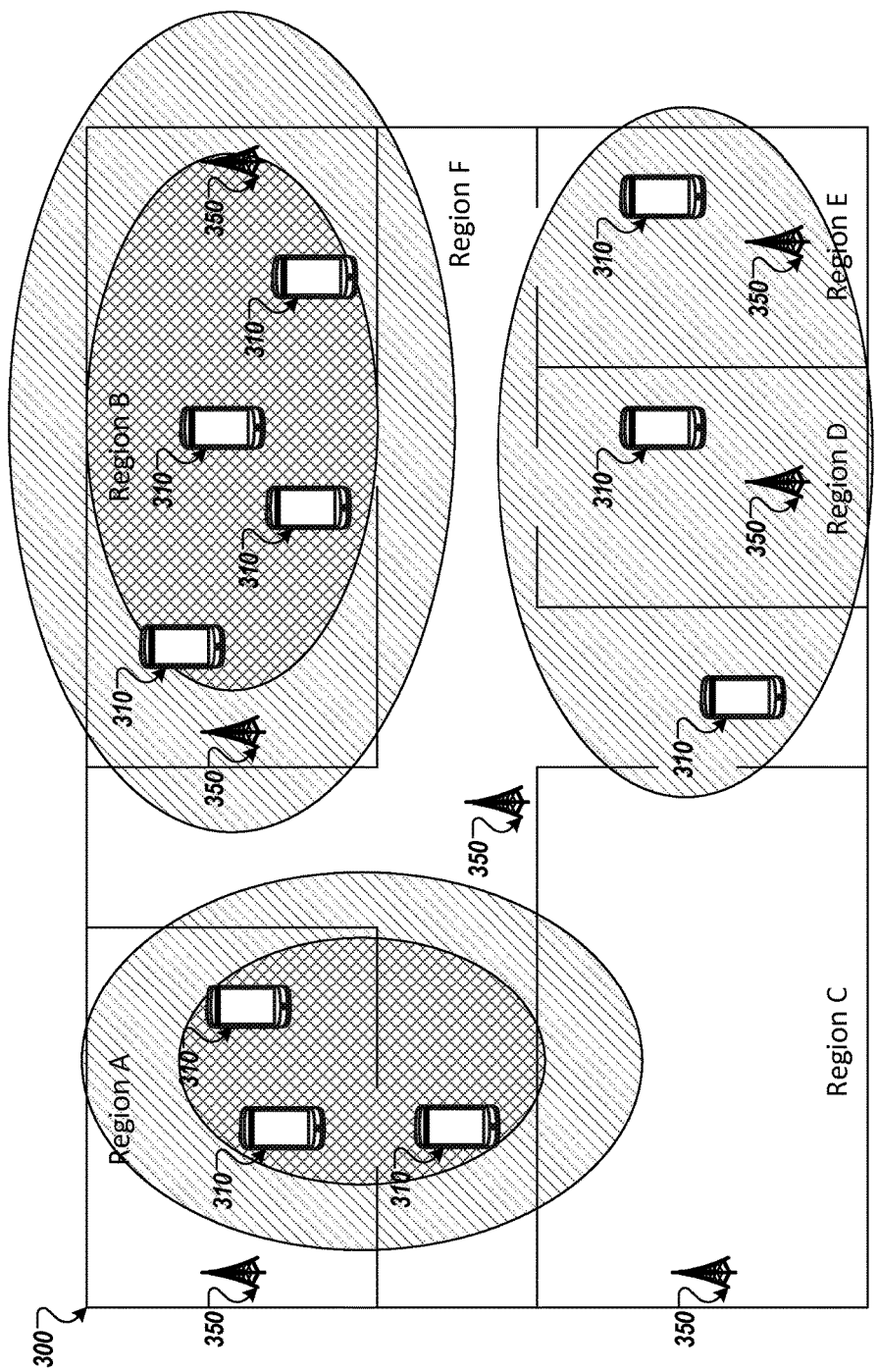
FIG. 3 depicts an example system for using proximity detection technology to determine client device population density.

FIG. 3 illustrates an example use of the estimated locations of one or more client devices, in which the estimated locations of multiple client devices is used to generate an occupation density map for the space. As shown in FIG. 3, the space 300 includes multiple wireless sensor beacons 350 that are positioned about the various regions A through F of the space 300. The space 300 is being occupied by multiple users each associated with a client device 310.

Using the described methods, the proximity detection system can estimate the locations of each of the client devices 310. Information identifying the estimated locations of each of the client devices 310 can be aggregated. For example, each of the client devices 310 can estimate their locations within the space 300 and can provide information to the location engine 130 identifying the estimated locations. In other implementations, each of the client devices 310 can transmit data to the location engine 130 identifying one or more wireless sensor beacons 350 and the proximity of a particular client device 310 to one or more of the wireless sensor beacons 350, and the location engine 130 can estimate the physical location of each of the client devices 310. Regardless of where the location estimation of each client devices 310 is performed, the information identifying the locations of the client devices 310 can be aggregated and analysis of the locations of the client devices 310 performed to determine the density of the client devices 310 in different areas or regions of the space 300. The location engine 130, one or more of the client devices 310, and or another system may then be able to access the aggregated location data for the space 300 to generate a graphic, such as that shown in FIG. 3, which illustrates the positions and density of the client devices 310 within the space 300.

In some instances, the density of client devices 310 within the space 300 may be determined by regions of the space 300. For example, the proximity detection system may determine the density of client devices 310 in each of regions A, B, C, D, E, and F separately. This density information may be presented graphically in a similar fashion as that shown in FIG. 3, and may further include presenting the estimated locations of one or more of the multiple client devices 310.

Figure 4:
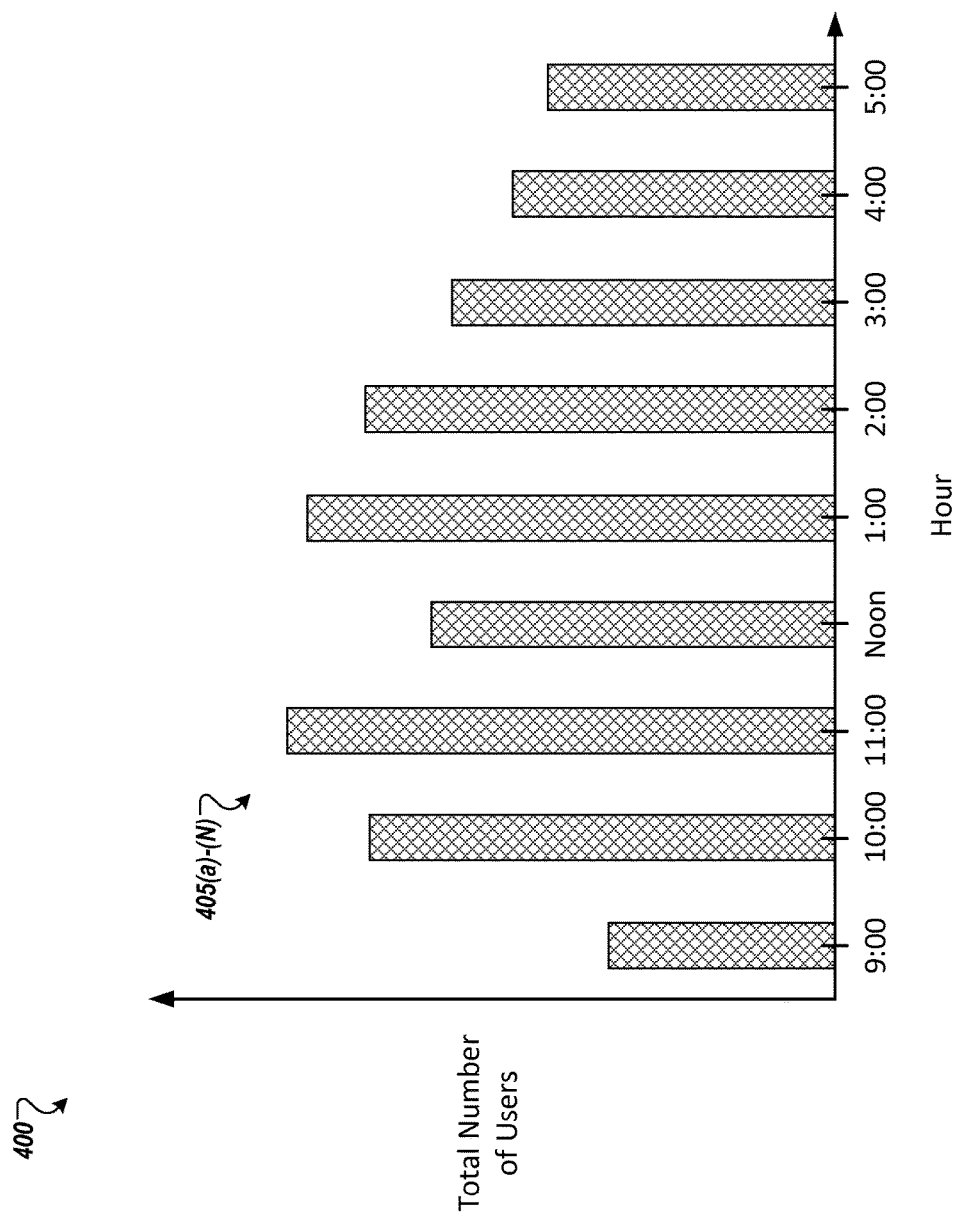
FIGS. 4-6 illustrate example analyses of data collected using proximity detection technology.

FIG. 4 illustrates a graphic in which the proximity detection system has tracked the presence of client devices within a space, or region of a space, over a period of time. For example, the graphic 400 may be a bar graph as shown, in which the graphic 400 describes the total number of unique client devices 310 present within the space 300 of FIG. 3 at various points in time.

Location information obtained from one or more client devices such as the client devices 310 may be received and/or determined for one or more points in time or time periods. For example, the location engine 130 may receive information from the client devices 310 of FIG. 3 that indicate the estimated locations of the client devices 310 at a particular point in time, e.g., at noon. The location engine 130 may determine the total number of client devices 310 present in the space 300 at the particular point in time, and may store information indicating the total number of client devices 310 present in the space 300 at the particular point in time. The location engine 130 may also receive and/or determine the total number of client devices present in the space 300 at other times, such as the number of client devices 310 in the space 300 at 9:00 AM, 10:00 AM, etc. In some implementations, the specific client devices detected as being located within the space 300 may change over time, for example, as users of the client devices 310 enter and exit the space 300. The location engine 130 can calculate the total number of client devices present in the space 300 for each of the selected time points, and can plot the total number of client devices present in the space 300 for each of the selected time points. The location engine 130 can plot the total number of client devices present in the space 300 over time using data points or graph bars 405(a)-(N) as shown in the graphic 400 of FIG. 4.

In some implementations, determining the total number of client devices present in a space can involve determining the total number of unique client devices that have been detected within the space for a predefined period, for example, the number of unique client devices 310 that have been detected in the space 300 from the time period extending from 11:00 AM to noon. Determining the total number of client devices present in the space during the time period may involve counting each client device only once during the time period, for example, such that any client device that was within the space during that period is counted, regardless of when the client device entered and/or exited the space during the time period, while also avoiding the counting of a particular client device within the space more than once for the time period.

Additionally, in some implementations, the graphic 400 may present information indicating the number of client devices located with a particular region of a property over time. For example, the graphic 400 may display the presence of client devices within region A of the space 300 over time. Additionally, while implementations described herein utilize the location engine 130 to perform the analysis required to produce the graphic of FIG. 4, in practice, other components of the proximity detection system may be utilized for such analysis. For example, a particular client device may receive information identifying the client devices present in a space or region of a space, and may compute the total number of client devices present in the space or in a region of the space at each of one or more time points or time periods. The client device may generate the graphic of FIG. 4 based on this analysis.

Figure 5:
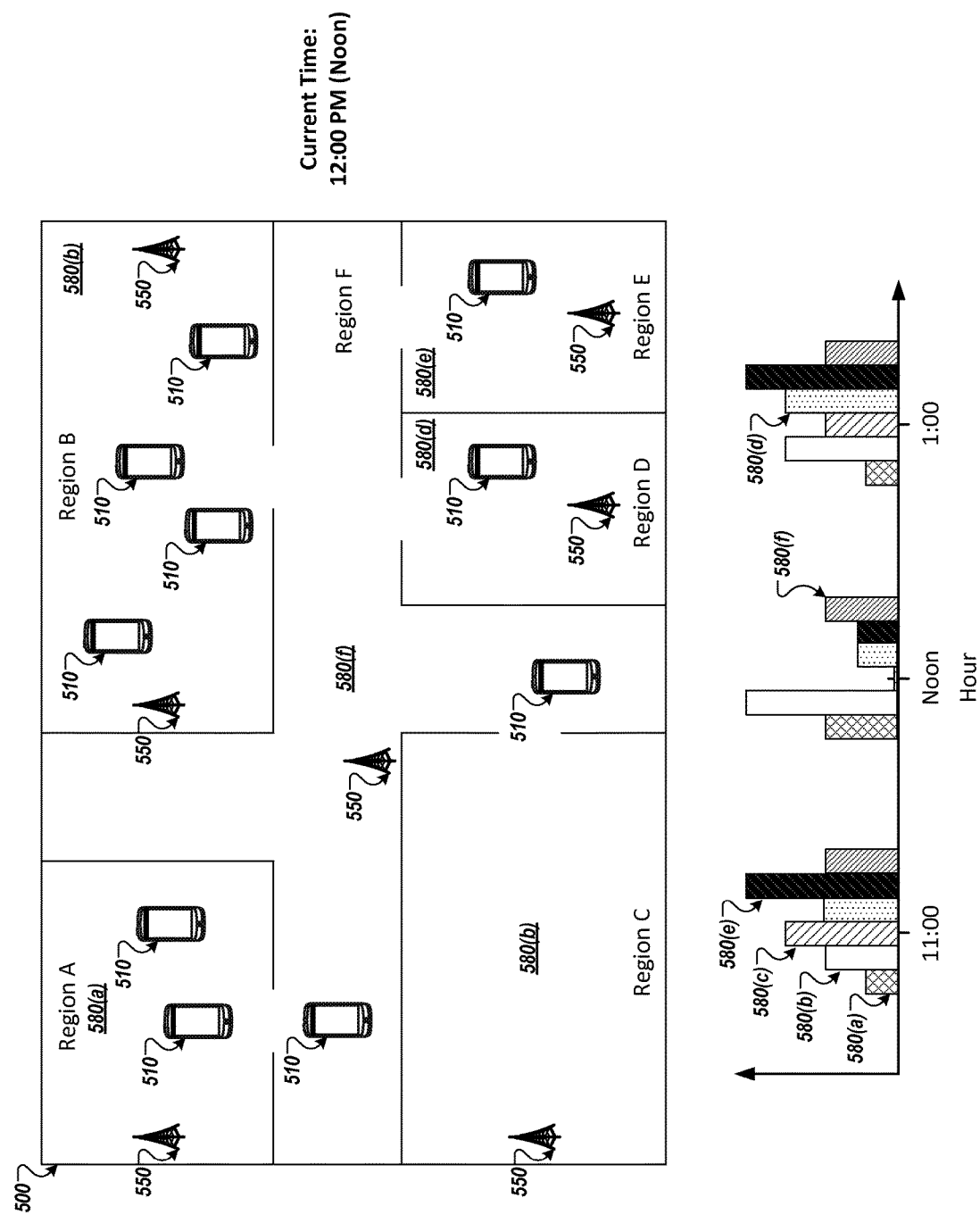

FIG. 5 illustrates another graphic that may be provided in association with the tracking of client devices 510 present within various regions 580(a)-(f) of the space 500. For example, the location engine 130 may receive information indicating the estimated locations of one or more client devices 510 at a particular point in time, for example, noon. Based on the estimated locations of the client devices 510, the location engine 130 may determine the number of client devices 510 present in one or more regions 580(a)-(f) of the space 500 at a particular time. The location engine 130 may then be able to produce a graphic that shows the estimated locations of the client devices 510 within the space 500 at the particular time. The location engine 130 may further be able to plot the number of client devices 510 within each region 580(a)-(f) of the space 500 over time. For example, FIG. 5 displays the estimated locations of client devices 510 within the space 500 at noon, and also displays a plot, shown in FIG. 5 as a bar graph, indicating the number of client devices 510 present in each region 580(a)-(f) of the space 500 at noon. As shown in FIG. 5, for example, the plot reflects that at noon there are two client devices 510 with estimated locations in region A, 4 client devices 510 with estimated locations in region B, zero client devices 510 with estimated locations in region C, one client device 510 with an estimated location in each of regions D and E, and two client devices 510 with estimated locations in region F. As described with respect to FIG. 4, the graphics shown in FIG. 5 may reflect the presence of client devices within regions of a space at a particular time, e.g., at noon, or within a particular range of time, e.g., 11:00 AM to noon.

Additionally, the location engine 130 may be capable of tracking the presence of client devices 510 within the regions 580(a)-(f) of the space 500 over time, such that the number of client devices 510 within each region 580(a)-(f) may be tracked over time. For example, FIG. 5 shows the populations in each of the regions 580(a)-(f) for the times 11:00 AM, noon, and 1:00 PM. While described herein as being performed by the location engine 130, in other implementations, other components of the proximity detection system (e.g., the client devices 510) may be capable of tracking and analyzing the estimated locations of one or more client devices 510 within the space 500 or regions of the space 500.

Figure 6:
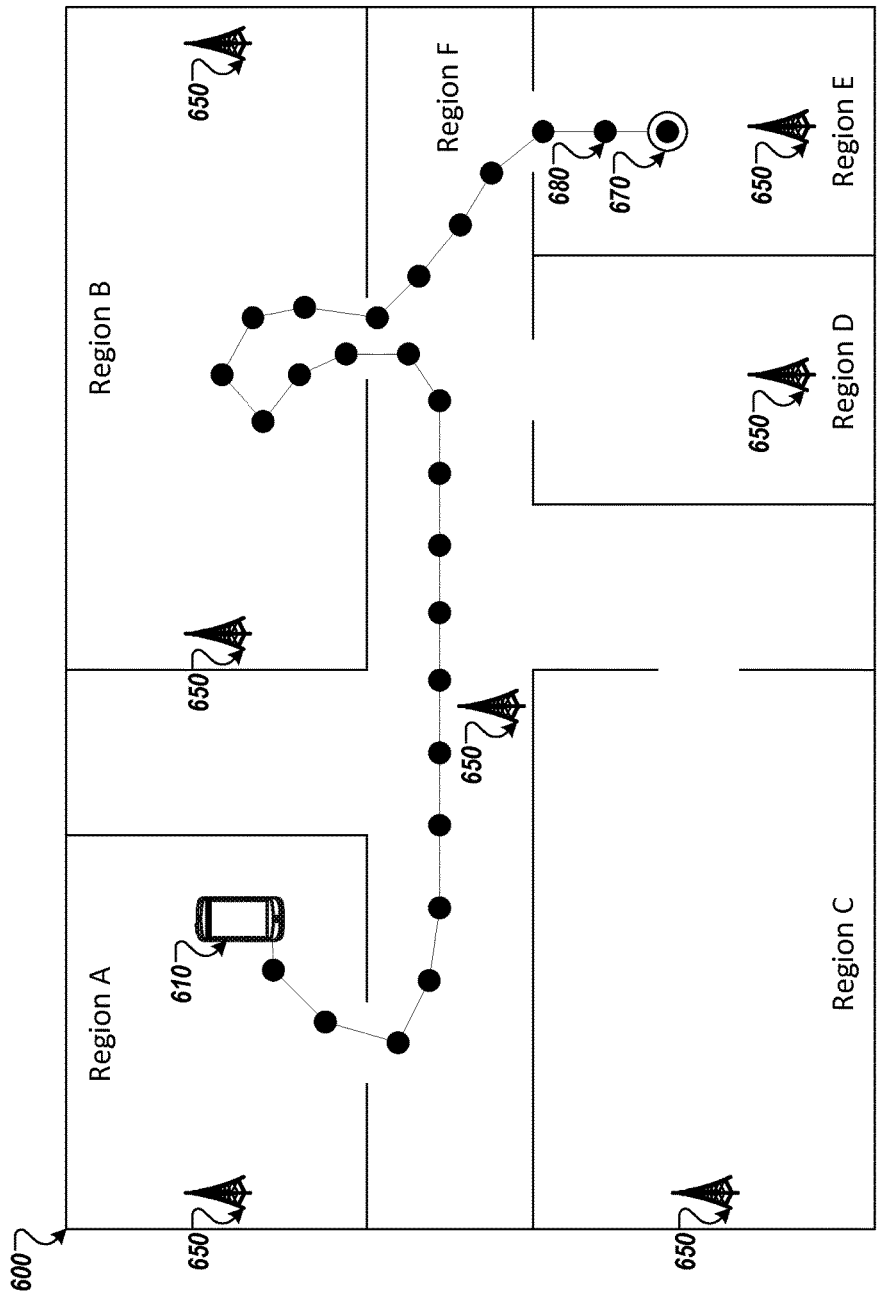

FIG. 6 illustrates an implementation of the proximity detection system that enables the tracking of a particular client device within a space over time. For example, the location of a client device 610 can be estimated at various time points, and a path of the client device 610 can be determined based on the locations of the client device 610 at the various time points.

Specifically, the proximity detection system can identify an initial estimated location of a client device 610, indicated by the point 670 of FIG. 6. This point can correspond, for example, to a time when the client device 610 first detected the presence of one or more wireless sensor beacons 650 and entered ranging mode to determine an estimated location of the client device 610. The proximity detection system can then identify subsequent estimated locations of the client device 610 that are each associated with a particular time. The estimated locations of the client device 610 can be mapped based on the estimated locations of the client device 610 at each time, or a subset of the times. In some implementations, a direction (e.g., a compass heading) and/or a rate of movement of the client device 610 can be determined based on the estimated locations of the client device 610 at each time. The aggregation of the estimated location data pertaining to the client device 610 and/or the plotting of the movement of the client device 610 as shown in FIG. 6 may be performed by the location engine 130 or by another component of the proximity detection system, for example, by the client device 610. Information used to generate the plot of the movement of the client device 610 may further be combined with information used to plot the movement of other client devices, to generate a mapping showing the movement of different client devices through the space 600 over time.

Additionally, in some implementations, the proximity detection system can maintain a mapping of the space 600, for example, a floor plan of the space 600 that identifies multiple regions A through F. In such implementations, tracking the movement of a client device 610 may involve confining the movements of the client device 610 to acceptable paths. For example, the proximity detection system 610 may prohibit a path of the client device 610 that travels through walls of the space 600 (e.g., where the proximity detection system has a map of the space 600 that defines the locations of walls in the space 600). If a detected path of the client device 610 does not match an acceptable path through the space 600, the proximity detection system may "snap" the path of the client device 610 to an acceptable path. Additionally or alternatively, the proximity detection system may maintain a history of paths of client devices through the space 600, and may determine the acceptable or expected paths of a client device 610 through the space 600 based on the history of paths taken by other client devices through the space 600.

Figure 7:
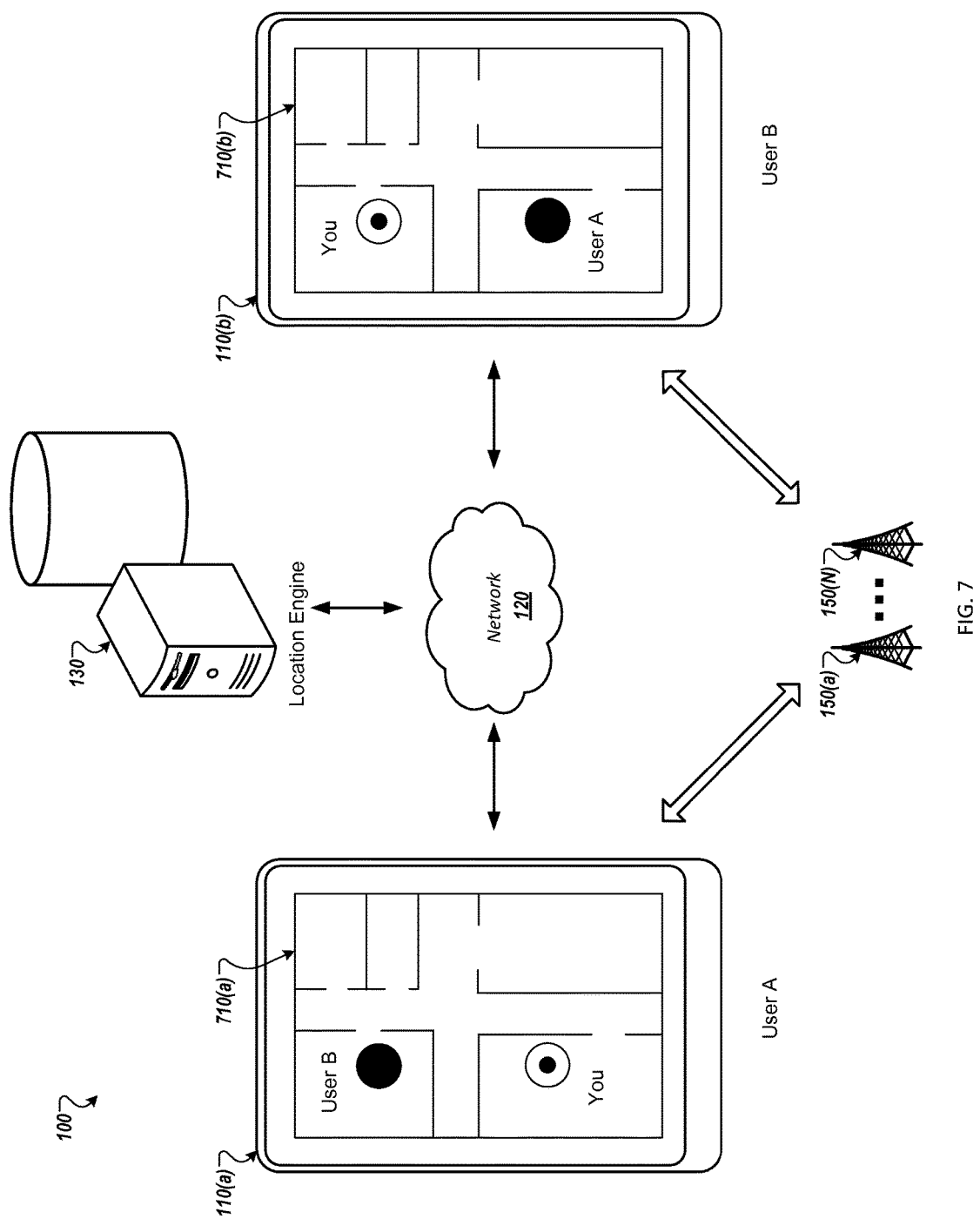
FIG. 7 depicts a system for interactions between multiple client devices based on proximity detection technology.

As described, in implementations in which two or more client devices are located within the same space or region, or are otherwise in communication with the proximity detection system (e.g., in communication with the location server 130), information relating to one client device or a user of the client device may be provided to another client device. FIG. 7 shows an example of such an application.

For example, information may be provided to a client device 110(a) associated with user A that relates to another client device 110(b) associated with a user B, or that relates to the user B. Information associated with a particular client device that is provided to other client devices can include information specifying the estimated location of the particular client device and/or a history of estimated locations of the particular client device. The information may further include information identifying the particular client device. For example, the information may include an identifier used specifically by the proximity detection system to uniquely, and, in some implementations, anonymously, identify any of the particular client device 110(a)-110(b), an instance of an application hosted on the particular client device 110(a)-(b), a user associated with the particular client device 110(a)-(b), a user profile associated with the particular client device 110(a)-(b), etc. Other information associated with a client device, a user of the client device, or a user profile associated with the client device, may be provided to other client devices. For example, information identifying a specific characteristic of other users may be provided to the other client device. Such characteristics may include, for example, an age of a user, a gender of a user, an expertise of the user, a user's contact information or information identifying a profile (e.g., a social network profile) of the user, information associated with the profile of the user (e.g., the user's calendar, affiliations, etc.), or other information.

The communication of information between the client devices 110(a)-(b) of FIG. 7 can be achieved via the network 120 and the location engine 130. For example, the client devices 110(a)-(b) can each be in communication with the location engine 130 over the network 120. Each client device 110(a)-(b), upon detecting and identifying the wireless sensor beacons 150(a)-(N), can notify the location engine 130 of its detection of the wireless sensor beacons 150(a)-(N), and/or may report an estimated location of the client device 110(a)-(b) to the location engine 130. The location engine 130 can determine that the client devices 110(a)-(b) are in the same space, for example, by determining that the client devices 110(a)-(b) are in a similar location or have identified wireless sensor beacons 150(a)-(N) having the same UUID or major identifier. Based on this determination, the location engine 130 can identify relevant information to provide to each of the client devices 110(a)-(b). Such information may include information relating to other client devices 110(a)-(b) and/or may include other information, such as particular content or information determined to be relevant to the estimated locations of the one or more client devices 110(a)-(b).

Figure 8:
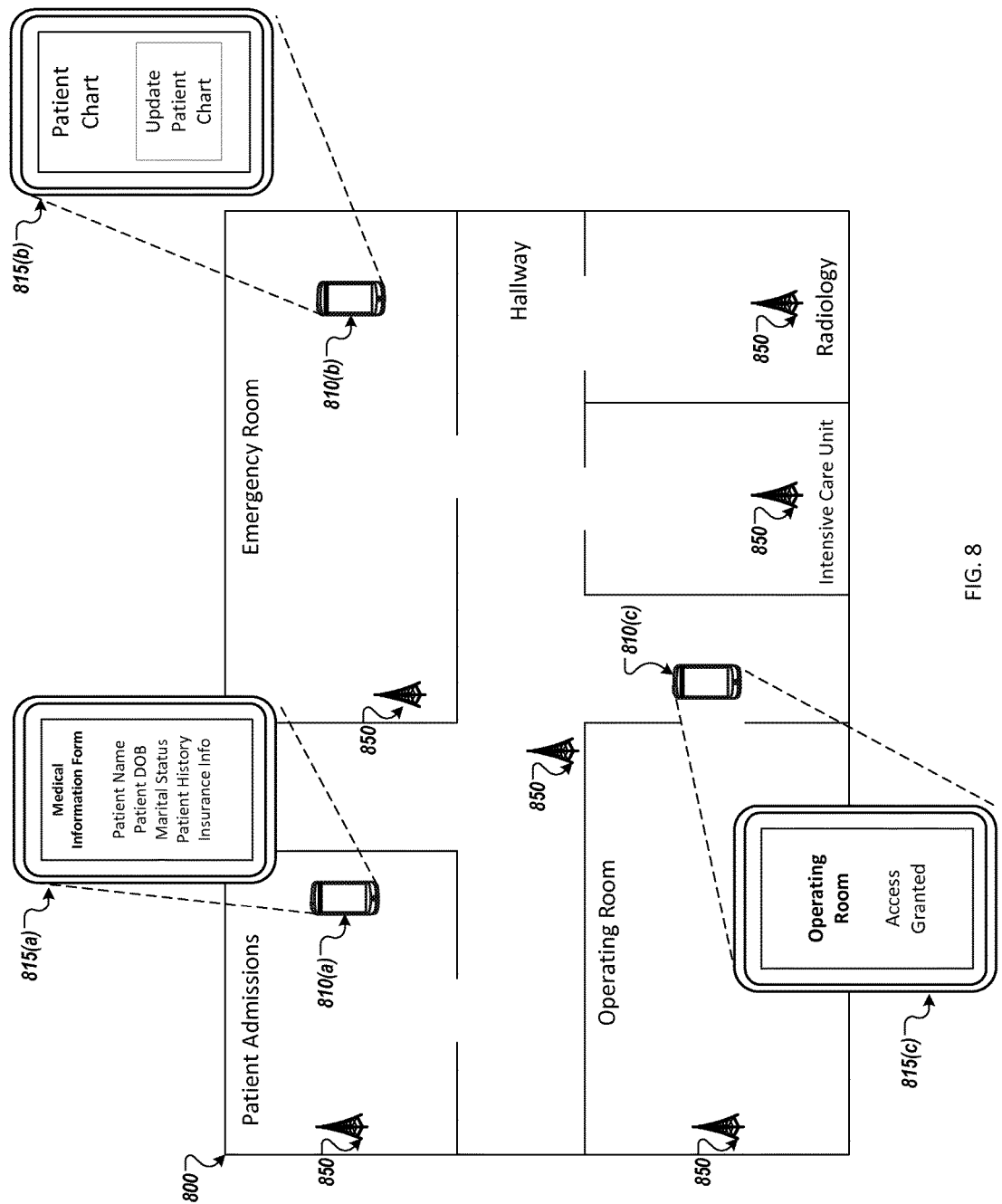
FIGS. 8-9 depict example systems for providing location-based healthcare information or services using proximity detection technology.

FIG. 8 illustrates an example system for providing location-based healthcare services and information to users of client devices via a healthcare proximity detection system. For example, a healthcare facility 800 may be associated with a proximity detection system that includes one or more wireless sensor beacons 850. Users that are associated with client devices 810(a)-810(c) may be provided with location-based services or information based on the healthcare proximity detection system determining that a client device 810(a)-810(c) is located in a particular location or region of the healthcare facility 800. Providing location-based services or information may include, for example, providing a client device 810(a)-810(c) with specific healthcare information, patient documents, or medical emergency notifications based on determining that the client device 810(a)-810(c) is located in a particular location or region of the healthcare facility 800, may include providing a user of the client device 810(a)-810(c) with the ability to perform certain actions, including custom actions that are unique to the healthcare facility 800 or the healthcare proximity detection system, or may include providing a user of the client device 810(a)-810(c) with access to secured locations or regions of the healthcare facility 800.

For example, the healthcare proximity detection system may determine that a client device 810(a) is located in a patient admissions department of the healthcare facility 800. The healthcare proximity detection system may determine that the client device 810(a) is located in patient admissions of the healthcare facility 800 based on, for example, determining that the client device 810(a) is proximate to a wireless sensor beacon 850 located in the patient admissions department of the healthcare facility 800. Based on determining that the client device 810(a) being identified as located in patient admissions of the healthcare facility 800, the healthcare proximity detection system can determine specific healthcare information, patient admissions forms, or a notification based on patient symptoms to present at a display or other interface 815(a) of the client device 810(a). For example, as shown in FIG. 8, a notification may be provided for output at the interface 815(a) that includes a medical information form for a patient that is associated with the client device 810(a). For instance, the medical form may include information required to admit the patient into the healthcare facility 800 such as patient name, patient date of birth, medical history, or medical insurance information. Such information may be presented automatically at the interface 815(a), or may be presented in response to a patient interaction with the client device 810(a), for example, based on a patient providing input to the client device 810(a) that indicates that the location of the client device 810(a) is near the wireless sensor beacon 850 within the healthcare facility 800.

In some instances, the interface 815(a) may also be displayed on the second device operated by a medical receptionist and/or healthcare provider. For example, in response to the wireless sensor beacon 850 determining that a patient has entered the patient admissions department of the healthcare facility 800 based on detecting the nearby client device 810(a) associated with the patient, a second interface including information displayed on the interface 815(a) may be presented on a hospital computer operated by a medical receptionist of healthcare professional. In such an example, patient information may be transmitted to the hospital computer based on the wireless sensor beacon 850 detecting a nearby client device 810(a) associated with a patient to be admitted into the healthcare facility 800.

Similarly, the healthcare proximity detection system may determine that the client device 810(b) is located in or near an emergency room of the healthcare facility 800. For example, the healthcare proximity detection system may determine that the client device 810(b) is most proximate to a wireless sensor beacon 850 that is located in emergency room of the healthcare facility 800, and may therefore determine that the client device 810(b) is likely located in the emergency room of the healthcare facility 800. Alternatively, the healthcare proximity detection system may estimate a physical location of the client device 810(b) by performing a trilateration or multilateration process that is based on the proximity of the client device 810(b) to each of multiple wireless sensor beacons 850 that are each associated with physical locations within the healthcare facility 800. Based on determining that the client device 810(b) is likely located in the emergency room of the healthcare facility 800, the healthcare proximity detection system may determine to provide a user of the client device 810(b) to perform a custom action. As shown in FIG. 8, for instance, the user of the client device 810(b) that is a healthcare provider such as a physician or an emergency medical technician may be presented with an option at an interface 815(b) of the client device 810(b) to "update patient chart" of a patient that is admitted to the emergency room of the healthcare facility 800. The interface 815(b) may include patient vitals such as heart rate, blood pressure, blood sugar, and/or other relevant biometric data related to the patient's current medical condition. The healthcare provider associated with the client device 810(b) may receive option to "update patient chart" to update patient treatment (e.g., treating a patient with particular antibiotics to prevent infection), along with a control that the healthcare provider may select to update the patient chart. While the "update patient chart" action shown in FIG. 8 is one example of an action that the healthcare provider may perform, the healthcare provider may be prompted to perform other actions or interactions with the healthcare proximity detection system or other systems based on the healthcare proximity detection system determining that the client device 810(b) is located in the emergency room of the healthcare facility 800. For example, healthcare provider may be able to lookup the medical history of the patient, see emergency information related to an incident or injury, or other patients currently in in emergency room of the healthcare facility 800. In other examples, the healthcare provider may be able to provide their contact information to other individuals located in emergency room of the healthcare facility 800, or may be capable of performing many other actions.

In another example, the healthcare proximity detection system can determine that the client device 810(c) of FIG. 8 is located near an operating room of the healthcare facility 800, where the operating room of the healthcare facility 800 may be a secured (e.g., locked) region of the healthcare facility 800 restricted to individuals that are sterile and have the appropriate medical credentials to perform a medical operation. The healthcare proximity detection system, based on determining that the client device 810(c) is located near operating room of the healthcare facility 800 may determine whether a user associated with the client device 810(c) is permitted to access operating room of the property 800. For example, a hospital account associated with the client device 810(c) or the user associated with the client device 810(c) may indicate that the user of the client device 810(c) has a credential or other permission that enables the user associated with the client device 810(c) to access the secured operating room such as being a designated physician of the healthcare facility 800 to perform a medical operation. Based on determining that the client device 810(c) is permitted to access the secured operating room of the healthcare facility 800, the healthcare proximity detection system may present information at an interface 815(c) of the client device 810(c) that indicates that the user associated with the client device 810(c) may access the secured operating room. In some implementations, the healthcare proximity detection system may also perform other actions that enable the user associated with the client device 810(c) to access the secured operating room of the healthcare facility 800, for example, by unlocking an entrance to the secured operating room. Similarly, additional or different content may be provided at the interface 815(c) that informs and/or enables the user associated with the client device 810(c) to access the secured operating room of the healthcare facility 800. For instance, the healthcare proximity detection system may determine a physical representation of a credential, key, or other information that enables the user associated with the client device 810(c) to access the secured operating room. As an example, an entrance to the secured operating room may include a keyless entry system that requires a user to scan a quick response (QR) code, barcode, or other code that unlocks the entrance to the secured operating room. In response to determining that the client device 810(c) is proximate to the entrance of the secured operating room and that the user associated with the client device 810(c) is permitted to access the secured operating room, the healthcare proximity detection system may cause a QR code to be displayed at the interface 815(c) that can be used to unlock the entrance to the secured operating room.

In another example, the secure access mechanism of the wireless sensor beacon 850 may be used to limit access to restricted locations of a hospital that require authorized access such as a pharmacy. For instance, the wireless sensor beacon 850 may exchange communications with a nearby client device 810(c) to determine if the patient associated with the client device 810(c) has a prescription to obtain medication from the pharmacy. In such instances, the healthcare proximity detect system to verify if the patient associated with the client device 810(c) may obtain medications requiring prescriptions. In another instance, the wireless sensor beacon 850 may be used to provide access to the pharmacy during particular time periods. For example, the wireless sensor beacon 850 may provide conditional access based on the hours of operation of the pharmacy within the healthcare facility 800.

While several examples of actions or information that may be presented to a patient or healthcare provider associated with a client device 810(a)-810(c) have been presented, other information or actions may also be triggered based on the healthcare proximity detection system determining that a client device 810(a)-810(c) is located in a particular region of the healthcare facility 800, is proximate to a particular wireless sensor beacon 850 associated with the space 850, or has a certain physical location within the healthcare facility 800. For example, based on a client device 810(a)-810(c) being identified as being in a certain region or physical location of the healthcare facility 800, or proximate to a certain wireless sensor beacon 850, a medical document may be transmitted to the client device 810(a)-810(c) for display at an interface 815(a)-815(c) of the client device 810(a)-810(c). In some instances, such a medical document may only be accessible when the client device 810(a)-810(c) is determined to be located in the certain region or physical location of the healthcare facility 800, or proximate to certain wireless sensor beacon 850. For instance, a patient or healthcare provider associated with a client device 810(a)-810(c) may only be permitted to access a certain sensitive document when the location of their client device 810(a)-810(c) is determined to be in a particular region of the healthcare facility 800. In some instances, a patient or healthcare provider associated with a client device 810(a)-810(c) may be provided with healthcare information indicating that they may or may not access such a medical document, or other content, based on the healthcare proximity detection system determining their location or proximity to certain wireless sensor beacons 850. For instance, if a medical document may only be accessed by a patient or healthcare provider associated with the client device 810(a) while they are located in patient admissions of the healthcare facility 800, the patient or healthcare provider may be presented at the interface 815(a) with healthcare information when they enter patient admissions that indicates that they now have access to the particular medical document or content. If the patient or healthcare provider attempts to access the medical document or content when they are not located in patient admissions of the healthcare facility 800, they may be presented with a notification indicating that they are not permitted to access the medical document or content at that time, but that they would be permitted to access the medical content or document if they were to move to patient admissions of the healthcare facility 800. If the patient or healthcare provider has already accessed the medical document or content while located in patient admissions, the patient or healthcare provider may also be presented with a notification at the interface 815(a) if they are nearing the edge of the patient admissions, for example, a notification that says "access to this medical document will be suspended if you leave this office."

In some examples, the action taken by a client device 810(a)-810(c) may be dependent upon the healthcare proximity detection system determining an action that a patient or healthcare provider of the client device 810(a)-810(c) is most likely to want or try to perform. For example, while a patient or healthcare provider of the client device 810(a) may be capable of performing a number of actions while located in patient admissions of the healthcare facility 800, such as access a document, determine a seminar that is occurring next in the patient admissions of the healthcare facility 800, or "update patient data" to patient admissions of the healthcare facility 800, the healthcare proximity detection system may determine that the patient or the healthcare provider is most likely to request what seminar is occurring next in the patient admissions, and may therefore determine to provide that information for display at the interface 815(*a*) of the client device 810(*a*), in lieu of, for example, presenting a certain medical document to the patient or healthcare provider at the interface 815(*a*).

In some examples, determining the action may involve evaluating one or more candidate actions to determine which action a user is most likely to want or try to perform while in the particular region or physical location of the healthcare facility 800, or while they are proximate to a specific wireless sensor beacon 850. For instance, each of multiple candidate actions may be associated with a relevance score that indicates the perceived relevance of particular actions to the particular region or physical location within the healthcare facility 800, or the perceived relevance of particular actions when a client device 810(*a*)-810(*c*) is proximate to a particular wireless sensor beacon 850. The relevance score may further indicate, for example, an estimated confidence of certain actions being relevant to the particular region, physical location, or wireless sensor beacon 850. In some instances, a relevance score may be based at least in part on history data that indicates actions that users of client devices 810(*a*)-810(*c*) have performed while in the particular region, physical location, or near the wireless beacon 850, such that the relevance score is influenced by past user behavior. The healthcare proximity detection system may determine an action to perform by selecting a particular action from among the candidate actions based at least in part on the relevance score of each of the candidate actions, or based on other information.

As an example, if history data indicates that a user associated with a client device 810(*a*)-810(*c*) is more likely to use their client device 810(*a*)-810(*c*) to log in to a computer system when they are located in a certain region of the healthcare facility 800 as opposed to accessing a document or desiring to "check-in" to the region of the healthcare facility 800, the relevance score for an action to log in to the computer system may be greater than the relevance scores associated with accessing a document or performing a "check-in" at the region of the healthcare facility 800. Based at least on the relevance scores for these candidate actions, the healthcare proximity detection system may determine to log the user associated with the client device 810(*a*)-810(*c*) into the computer system, and not to access a document or perform a "check-in" at the region of the healthcare facility 800.

In some examples, the healthcare proximity detection system may determine that two or more client devices 810(*a*)-810(*c*) that are associated with a single user must be present in certain locations or regions of the healthcare facility 800, or proximate to certain wireless sensor beacons 850, to enable an action. For example, a user may be associated with both a smartphone device and a smartwatch device that are each in communication with the healthcare proximity detection system. Certain actions may require that the smartphone device and smartwatch device are located in specific regions or locations of the healthcare facility 800, or proximate to a certain wireless sensor beacon 850 to allow the actions to be performed. Alternatively, certain actions may require that the smartphone device and smartwatch device be in the same region or location of the healthcare facility 800, or proximate to the same wireless sensor beacon 850, for the actions to be performed. For example, for the user to access a certain document using their smartphone device, the healthcare proximity detection system may require that both the smartphone and smartwatch devices associated with the user are located in patient admissions of the healthcare facility 800. The healthcare proximity detection system may determine whether both the smartphone and smartwatch devices are located within the patient admissions of the healthcare facility 800, and if both devices are not determined to be located in the patient admissions of the healthcare facility 800, access to the document may be prohibited. In a similar example, accessing the document using the smartphone may require that the smartphone and smartwatch are located in the same region or physical region of the healthcare facility 800, or are proximate to the same wireless sensor beacon 850. Upon the user requesting to access the document using the smartphone, the healthcare proximity detection system may determine the regions or physical locations where each of the smartphone and smartwatch are located, or may determine the wireless sensor beacon 850 nearest to each of the smartphone and smartwatch. Access to the document using the smartphone may be permitted if the healthcare proximity detection system determines that the two devices are located in the same region of the healthcare facility 800, if the physical locations of the smartphone and smartwatch are within a threshold proximate distance of one another, or if the smartphone and smartwatch are nearest to the same wireless sensor beacon 850.

Figure 9:
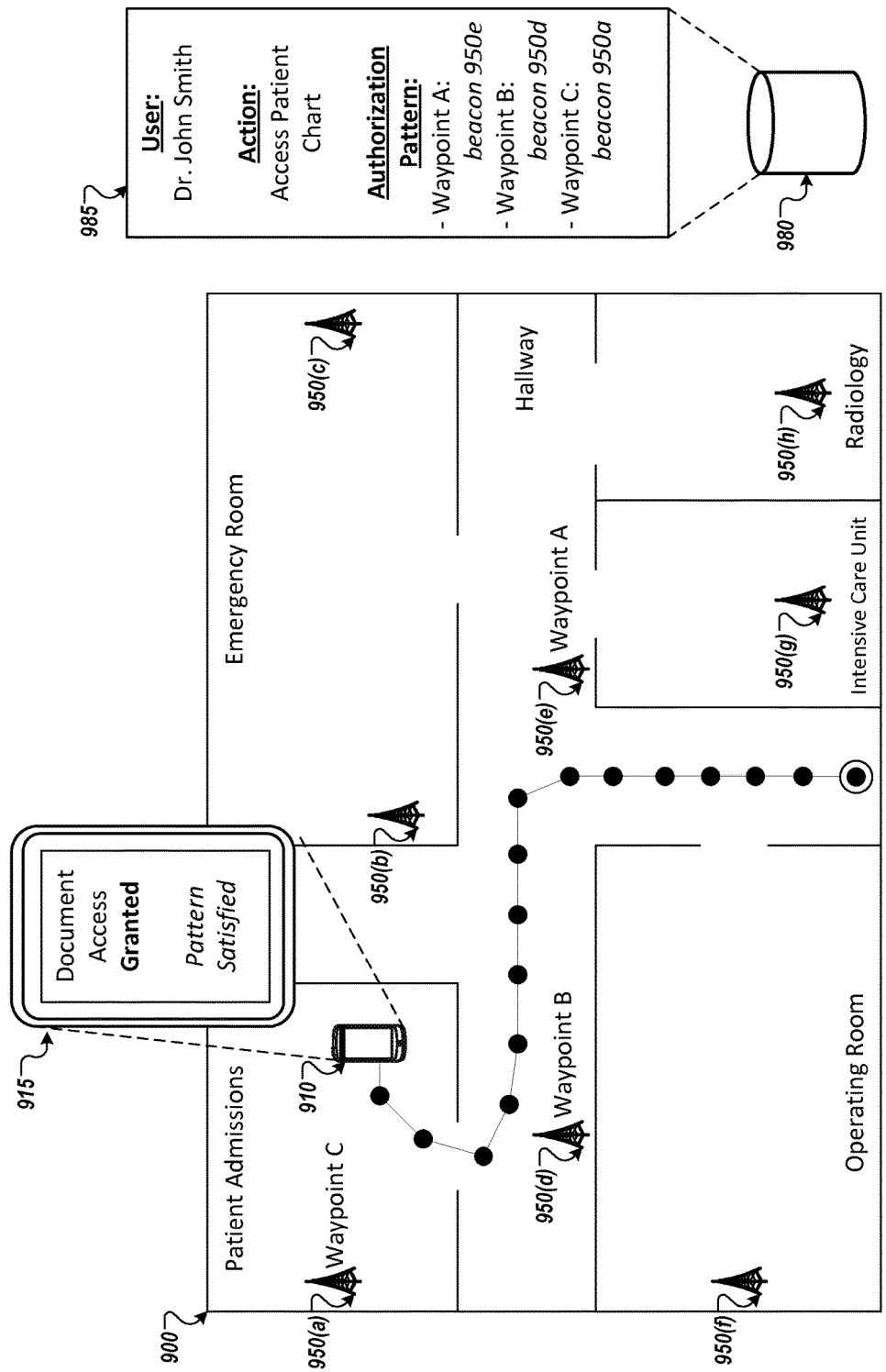

FIG. 9 illustrates another example system for providing location-based services and content to a user associated with a client device 910. In some implementations, as shown in FIG. 9, for a user associated with a client device 910 to perform a certain action, the healthcare proximity detection system must first determine that a path of movement of the client device 910 satisfies a pattern of movement that is associated with performing the action.

For example, the healthcare proximity detection system may include a database 980 that stores one or more patterns 985 that are each associated with a particular user, client device, and/or action. For example, the pattern 985 shown in FIG. 9 may be specific to the user "John Smith" associated with the client device 910. The pattern 985 may require the client device to follow a path that includes waypoints before the "John Smith" is permitted to perform the action of accessing a document using the client device 910. Specifically, as shown in FIG. 9, the pattern 985 may require that the client device 910 pass each of waypoint A, corresponding to wireless sensor beacon 950(*e*), waypoint B, corresponding to wireless sensor beacon 950(*d*), and waypoint C, corresponding to wireless sensor beacon 950(*a*) before the user is permitted to access a document using the client device 910. In some implementations, for the pattern 985 to be satisfied, the healthcare proximity detection system may require that the path of movement of the client device 910 satisfies each of the waypoints in order (i.e., that the path of movement proceed from waypoint A to waypoint B and then to waypoint C), or may not require that the path of movement of the client device 910 satisfy each of the waypoints in a particular order, but only that each waypoint must be satisfied. In some examples, satisfying a waypoint may involve determining that a location of the client device 910 is within a certain region of the hospital 900, that a physical location of the client device 910 determined by the healthcare proximity detection system is within a threshold distance of a particular wireless sensor beacon 950(*a*)-950(*h*), or that the client device 910 is within a threshold proximity of a wireless sensor beacon 950(*a*)-950(*h*).

Following the example shown in FIG. 9, the user "John Smith" may enter the hospital 900 and the healthcare proximity detection system may begin tracking a path of movement of the client device 910 associated with the user. Tracking the path of movement of the client device 910 may be performed, for example, using the methods discussed with respect to FIG. 6. Upon entering the hospital 900, the client device 910 may be detected as passing near the wireless sensor beacon 950(e) corresponding to the waypoint A. For example, the waypoint A may be located near a lobby or security checkpoint in the hospital 900 that the user must pass when entering the hospital 900. The healthcare proximity detection system may further determine that the client device 910 has passed the wireless sensor beacon 950(d) corresponding to waypoint B. and then determine that the client device 910 has passed the wireless sensor beacon 950(a) corresponding to waypoint C. Based on determining that the path of movement of the client device 910 has satisfied each of the waypoints provided for in the pattern 985, the healthcare proximity detection system may determine that the user "John Smith" is permitted to perform the action of accessing a document using the client device 910. In response to the determination, the healthcare proximity detection system may optionally provide a notification at an interface 915 of the client device 910 indicating that the pattern 985 has been satisfied. For example, the notification "Document Access Granted" may be presented at the interface 915 in response to determining that the path of movement of the client device 910 has satisfied the pattern 985.

In some implementations, the pattern 985 may be predetermined and stored in the database 980 of the healthcare proximity detection system. For example, the pattern 985 may be specified by one or more administrators associated with the healthcare proximity detection system. Additionally or alternatively, the pattern 985 may be determined based on tracking the movement of the client device 910 over time. For example, based on determining that the client device 910 typically passes by each of the waypoints A, B, and C before the user "John Smith" attempts to access a document using the client device 910, the healthcare proximity detection system may establish as the pattern 985 the waypoints A, B, and C as shown in FIG. 9. In some examples, a pattern 985 may be updated or evolve over time, for example, based on determining that more waypoints are needed to ensure that the path of the client device 910 satisfied the path that is intended to be required of the client device 910 before the client device 910 is granted permission to perform the action. In another example, if the healthcare proximity detection system determines that, over time, a user associated with the client device 910 follows a different path before attempting to perform the action, the healthcare proximity detection system may update the pattern 985 to match the new path.

In some instances, requiring that a path of movement of the client device 910 must satisfy a pattern 985 before permission to perform a particular action is granted allows for additional security, as attempts to perform the action where the client device 910 has not satisfied the pattern 985 may indicate a fraudulent attempt to perform the action, an error with the healthcare proximity detection system or the client device 910, or other events or anomalies, such as a user working in a different area than they typically work in an office building. Such event or anomaly detection may also be used outside of the context of gaining permission to perform certain actions. For example, the healthcare proximity detection system may monitor paths of movement of one or more client devices and may be able to detect anomalous events, such as emergencies, based on the path of movement of the one or more client devices. For example, based on determining that a number of client devices follow a path toward an exit of a building at the same time, where such movement is not typical, the healthcare proximity detection system may determine that a possible emergency (e.g., a fire) has occurred in the building, and may react to the determination (e.g., by notifying the authorities, sounding a fire alarm, etc.).

Figure 10:
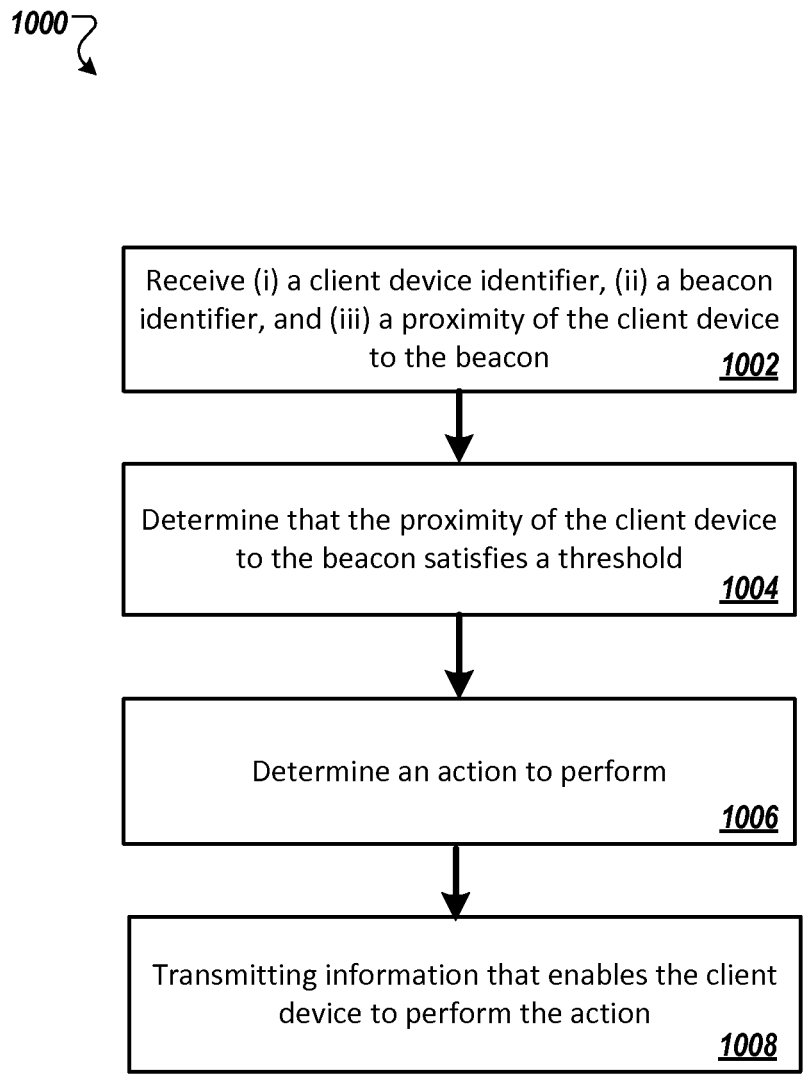
FIG. 10 depicts an example process related to providing location-based healthcare information or services using proximity detection technology.

FIG. 10 illustrates an example process 1000 for providing location-based services and information to a client device using a healthcare proximity detection system. In some examples, the process 1000 may be performed by the healthcare proximity detection system 100 of FIG. 1.

Information is received that indicates a client device identifier associated with a client device, a beacon identifier associated with a wireless sensor beacon, and a proximity of the client device to the wireless sensor beacon (1002). For example, the location engine 130 of FIG. 1 may receive information from a client device 110(a)-110(b) that is running an instance of a healthcare proximity detection system application that includes an identifier that uniquely identifies a client device 110(a)-110(b), that includes an identifier that uniquely identifies a wireless sensor beacon 150(a)-150(N) in the healthcare proximity detection system 100, and that indicates a proximity of the identified client device 110(a)-110(b) to the identified wireless sensor beacon 150(a)-150(N). In some implementations, the information may be received by the location engine 130 over the one or more networks 120. The information indicating the proximity of the client device 110(a)-110(b) to the wireless sensor beacon 150(a)-150(N) may be received from the client device 110(a)-110(b), or alternatively may be computed by the location engine 130, for example, based on receiving information that indicates a strength of a wireless signal emitted by the wireless sensor beacon 150(a)-150(N) detected by the client device 110(a)-110(b).

A determination is made that the proximity of the client device associated with the client device identifier to the wireless sensor beacon associated with the beacon identifier satisfies a threshold proximity (1004). For example, the location engine 130 may receive or determine the proximity of the identified client device 110(a)-110(b) to the identified wireless sensor beacon 150(a)-150(N), and may compare the proximity to a threshold. The proximity threshold may be a predetermined proximity threshold, such as one set by an administrator of the healthcare proximity detection system, or may be a proximity threshold that is otherwise determined. For example, the proximity threshold may be determined based on a machine learning process that optimizes the proximity threshold based on tracking performance of the healthcare proximity detection system 100 for various proximity thresholds. The location engine 130 may determine that the proximity of the client device 110(a)-110(b) to the wireless sensor beacon 150(a)-150(N) satisfies the proximity based on, for example, determining that the proximity is less than the proximity threshold, thereby indicating that the client device 110(a)-110(b) is within a threshold proximity of the identified wireless sensor beacon 150(a)-150(N).

Based on determining that the proximity of the client device associated with the client device identifier to the wireless sensor beacon associated with the beacon identifier satisfies the threshold, an action to be performed is determined (1006). For example, based on the location engine 130 determining that the client device 110(a)-110(b) associated with the client device identifier is within the threshold proximity of the identified wireless sensor beacon 150(*a*)-150(N), the location engine 130 can determine an action for the identified client device 110(*a*)-110(*b*) to perform. For example, the determined action may be an action to present or provide access to a document or other content, to provide a notification, to grant access to a particular region, location, or other area of a property or other space, to perform a custom action, to request information from a user, or to perform another action. In some examples, determining the action to perform may involve determining an action that the client device 110(*a*)-110(*b*) is otherwise permitted to perform, for example, based on a path of movement of the client device 110(*a*)-110(*b*) satisfying a specific movement pattern as discussed with respect to FIG. 9. In some examples, the determined action may be determined based on the wireless sensor beacon 150(*a*)-150(N) that the client device 110(*a*)-110(*b*) is determined as being proximate to. For example, the location engine 130 may determine one action based on the client device 110(*a*)-110(*b*) being proximate to a particular wireless sensor beacon 150(*a*)-150(N), and may determine another action based on the client device 110(*a*)-110(*b*) being proximate to another wireless sensor beacon 150(*a*)-150(N).

Information is transmitted to the client device associated with the received client device identifier that enables the client device to perform the action (1008). For example, the location engine 130 may provide information to the identified client device 110(*a*)-110(*b*) that causes or enables the identified client device 110(*a*)-110(*b*) to perform the determined operation. In some instances, the information may be provided over the one or more networks 120 of the proximity detection system 100. The identified client device 110(*a*)-110(*b*) may receive the information enabling performance of the determined action, and in response may perform the action.

The described methods can be implemented in any number of different settings where it would be useful to have capabilities to track the location of one or more client devices, and to access and share additional information among the client devices that relates to users of the client devices or to the client devices themselves.

For example, a proximity detection system may be associated with a hospital, medical office, or other space associated with providing healthcare services. The proximity detection system associated with the space may provide services to patients, doctors, nurses, staff, or other visitors or personnel that are visiting or working at the hospital, medical office, or other space. In some implementations, one or more of these groups of people (e.g., patients or doctors) may utilize a specific application hosted by their client devices that is associated with the proximity detection system. The group-specific applications may provide services that are specific to that group. For example, patients may use a patient-specific version of an application that is hosted on their client devices, while doctors, nurses, staff, emergency responders, or other medical personnel may use a healthcare provider-specific version of an application that is hosted on their client devices. The services provided by the patient application and the healthcare provider application may be different, or both applications may provide some or all of the same services.

In some implementations, the proximity detection system associated with a hospital, medical office, or other space associated with providing healthcare services may have access to information relating to various patients, doctors, or other personnel working at the hospital. The proximity detection system may also be able to access scheduling or other information associated with the hospital, medical office, or other space associated with providing healthcare services, such as a schedule of appointments for a particular doctor's office or what kind of procedures are performed by a doctor associated with the doctor's office. The proximity detection system may be able to access other information associated with the hospital, medical office, or other space associated with providing healthcare services, for example, a map of a hospital, information indicating where various services are offered in a hospital (e.g., where a radiology department is located in a hospital), or other information. In some instances, the information accessed by the proximity detection system is available over one or more networks, such as the network 120. For example, the location engine 130 or a client device 110(*a*)-(*b*) may be able to access such information over the network 120. Such information may be accessible, for example, at a healthcare provider server, patient database, website, or other resource that is accessible by the location engine 130 or client device 110(*a*)-(*b*) over the network 120. In some implementations, the location engine 130 may store such information locally, such that the client device 110(*a*)-(*b*) may access the information over the network 120. In still other implementations, the client device 110(*a*)-(*b*) may store such information locally. The proximity detection system can integrate such information with location information determined for a user (e.g., a patient's or a doctor's location) to provide various services to the user.

In some applications, patients or other visitors of a hospital, medical office, or other space associated with providing healthcare services may be provided with location-based services offered by the proximity detection system. The patients or other visitors may be provided these services by using a patient application hosted on their client devices. The proximity detection system may be able to determine the presence and/or movement of the patients or visitors within a hospital, medical office, or other space associated with providing healthcare services. Based on this location information and other information accessible by the proximity detection system, the proximity detection system can provide services useful to the patients or visitors.

In some instances, a patient or visitor may be able to check-in to an appointment at a hospital, medical office, or other space associated with providing healthcare services based on the proximity detection system determining that the user has arrived or is at a certain location near or within the hospital, medical office, or other space. For example, a proximity detection system may be associated with a doctor's office in a hospital, and the proximity detection system may be able to determine that a certain patient of the doctor has parked at the hospital, has entered the hospital, is near the doctor's office in the hospital (e.g., is on the same floor), or is in the doctor's office. The proximity detection system may additionally be able to determine that the patient has an appointment scheduled at the doctor's office at a time near the time when the patient is detected. The proximity detection system may then cause the patient to be checked-in for their appointment.

For example, the proximity detection system may report to a computer system associated with the doctor's office that the patient has arrived for their appointment and should be checked-in for their appointment. In some implementations, checking the patient in for the appointment can involve providing the computer system associated with the doctor's office with information about the patient, such as their personal information (e.g., name, address, emergency contacts, etc.) or medical history information (e.g., record of immunizations, allergies, reports of their last doctor's visit, etc.). The information provided to the computer system associated with the doctor's office may be information that the patient has provided to the proximity detection system and has authorized the proximity detection system to provide to the computer system associated with the doctor's office, or may be information that the proximity detection system can otherwise access and that the patient has authorized to be provided to the computer system associated with the doctor's office. For example, the proximity detection system can access the patient information at a healthcare provider database that stores information about various patients, and can forward such information to the computer system associated with the doctor's office. In some implementations, the proximity detection system can provide the patient information to the computer system associated with the doctor's office from a client device associated with the patient or from a location engine (e.g., the location engine 130) over one or more networks (e.g., the network 120). In some implementations, the computer system associated with the doctor's office can store the patient information locally on the computer system, such that the proximity detection system is only required to notify the computer system that the patient has arrived at the hospital or the doctor's office. In such an implementation, the check-in process may be completed by the computer system associated with the doctor's office and/or the computer system associated with the doctor's office may access the patient's information.

The proximity detection system may also enable a patient or visitor to access one or more areas of a hospital, medical office, or other space associated with providing healthcare services based on the patient's proximity to those areas. For example, a proximity detection system may allow the patient to enter the doctor's office when they are detected as being near the doctor's office, may allow the patient to enter a particular area of the doctor's office, such as a radiology area, particular examination room, etc., when they are near, or may enable the patient to enter another area of the hospital or doctor's office.

The proximity detection system may enable the patient to access a particular area based on determining that the patient has permission to access the area. For example, the proximity detection system may determine that a client device associated with the patient is hosting an instance of a patient application and is near an area that all users with client devices hosting the patient application are allowed to enter (e.g., a radiology department). Based on determining that the patient is near the area and is hosting the patient application on their client device, they may be provided with access to the area (e.g., a door leading to the area may be unlocked). In some implementations, the patient may be provided access to an area based on additional information accessed by the proximity detection system. For example, the patient may be provided access to a particular doctor's office in a hospital based on the proximity detection system determining that the patient is a patient of the doctor associated with the doctor's office, that the patient has an appointment at the doctor's office around a time when the patient is detected near the doctor's office, that the patient has been directed to the doctor's office by another doctor or personnel (e.g., that another doctor has referred or prescribed the patient to go to the doctor's office), and/or based on other factors. For example, the patient may be granted access to a doctor's office based on the proximity detection system determining that the patient has an appointment at the doctor's office that day and that the patient is near the doctor's office during a two-hour window corresponding to their scheduled appointment time.

In some implementations, a patient application hosted by a patient's client device may enable the patient to provide a healthcare provider with all or a relevant portion of their personal or medical history information. The patient may be able to send the information to particular recipients (e.g., particular doctors or nurses), may be able to send the information to recipients that are determined to be near the patient (e.g., a certain nurse that is in the same examination room as the patient), or may be able to send the information to a group of recipients with certain characteristics (e.g., all doctors and nurses that are helping the patient or all doctors within the same healthcare network). In some instances, the patient may be able to select information to provide to one or more recipients, for example, certain personal or medical history information, or may be able to provide the one or more recipients with all of their information.

In some implementations, recipients of patient information can request that the patient provide particular information (e.g., only a patient's contact information and allergy information) such that the patient can respond to the request with the particular information. For example, a doctor using an application associated with a proximity detection system can request information from a particular patient or a patient near them (e.g., in the same examination room), such that the patient can respond to the request using the patient application hosted by their client device.

In other implementations, the proximity detection system can provide a patient's information or a subset of their information to medical professionals that are near the patient. For example, the proximity detection system can determine the location of the patient and one or more doctors or nurses near the patient, and can provide all of the doctors or nurses near the patient with the patient's information. In some implementations, the proximity detection system can determine that a patient is arriving at or checking-in to a scheduled appointment, and may be able to provide all or a subset of their patient information as a part of the check-in process for the appointment. For example, the patient can be provided with a notification at their client device indicating that they have been checked-in for their appointment and requesting that the patient provide their information as a part of the check-in process for their appointment. In some implementations, patients may be able to update their personal information or other information (e.g., portions of medical history information) using the patient application hosted on their client devices. The use of a proximity detection system to enable the sharing and modification of a patient's personal and/or medical history information reduces the need for paper forms within a hospital, medical office, or other space associated with providing healthcare services.

In some implementations, the proximity detection system may enable a patient or healthcare provider (e.g., a doctor, nurse, or staff member) to document a patient's visit and/or information about the patient's visit. For example, a patient application hosted on the patient's client device can determine locations where the patient has been in a hospital, and can document where the patient traveled in the hospital during their visit (e.g., that the patient went to both a certain doctor's office and a radiology department in the hospital). In some implementations, the proximity detection system can determine the patient's location and can also determine tasks that the patient is supposed to complete (e.g., that the patient has been instructed to have x-rays taken). The proximity detection system may be able to determine if the patient has satisfied the tasks. For example, a doctor may instruct a patient to have x-rays taken at a radiology department of a hospital and to have a prescription filled at a pharmacy of the hospital. Based on the proximity detection system determining that the patient was located at the radiology department but was not located at the pharmacy, the proximity detection system may record the patient as having had the x-rays taken, and may also make record that the patient likely still needs to have their prescription filled. Other information may be recorded by the proximity detection system. For example, the proximity detection system may determine that the patient was with (e.g., was detected as being near) a certain doctor at a certain time and place in a hospital, and may document the patient's visit with that doctor. In some implementations, the patient and/or other users of the proximity detection system may be able to take notes relating to a patient's visit, document instructions or prescriptions for the patient that were provided during the visit, or update information associated with the patient. The notes or other documentation can be accomplished by using applications associated with the proximity detection system that are hosted by the patient's or other user's client device.

In some implementations, a patient application hosted by a patient's client device may provide additional location-based services to the patient. For example, based on the patient application determining that the user is likely trying to navigate to a particular location or area in a hospital, the patient application can determine the patient's current location and can provide navigation services directing the patient to the particular location. Determining that a patient is likely attempting to navigate to a particular location or area can include receiving input from the patient that specifies a destination location or area, determining that the patient has an appointment at the location or area, determining that the patient has been instructed to go to the location or area (e.g., to have x-rays taken at a radiology department), or based on other information accessible to the proximity detection system. Navigation services can include providing the patient with a map showing their location and/or their destination, directions from their current location to the destination, etc. Such a map can also be capable of providing navigation to other locations in the hospital, such as directions to information desks, security checkpoints, restrooms, restaurants, etc. In some implementations, if a patient is trying to locate a specific individual (e.g., their doctor), the patient may be provided with navigation information to the doctor based on the proximity detection system determining the locations of both the patient and the doctor.

While patients or other visitors of a hospital, medical office, or other space associated with providing healthcare services may use a patient application hosted by their client devices, healthcare providers or other individuals working at the hospital, medical office, or other space may use a healthcare provider application hosted by their client devices. A healthcare provider application may be used by any number of healthcare providers or other personnel, such as doctors, nurses, specialists, receptionists, staff, technicians, emergency responders, security personnel, or others. The healthcare providers and other personnel may be provided with specific services via the healthcare provider application.

For example, the healthcare provider application can enable a user to view navigation information, to determine where particular patients are located, which patients are in certain areas, which patients have arrived or are late for appointments, which healthcare provider(s) a patient is currently with, etc. For example, a user of a healthcare provider application may want to travel to a particular doctor's office in a hospital or may want to locate another facility in the hospital (e.g., the emergency room or a particular radiology department) and may be provided with navigation services directing the user to those locations. Such navigation services may direct the user from their estimated current location as determined by the proximity detection system to the destination location, based on the proximity detection system also being able to access a location of the user's destination.

In other implementations, a doctor may be associated with numerous patients that the doctor sees regularly or is currently caring for. The proximity detection system may be able to determine which of these patients are currently within a hospital where the doctor works and can determine locations of these patients. The healthcare provider application may enable the doctor to view a list of their patients that are currently at the hospital, or may enable the doctor to view the locations of one or more of those patients within the hospital. In some implementations, tracking which patients are present and/or the locations of those patients within the hospital may be dependent upon the patients granting permission for their locations to be tracked and/or granting permission for their locations to be reported to other users of the proximity detection system.

In another example, the proximity detection system may be able to determine the locations of one or more patients to determine which patients are in which rooms of a doctor's office. For instance, the doctor's office may have a wireless sensor beacon in each room, such that the proximity detection system can determine which patients are currently in each room. The proximity detection system associated with the doctor's office can determine which room each patient is in based on determining which wireless sensor beacon each patient is closest to, based on estimating a location of the patient using trilateration, or based on other methods. Based on this information the healthcare provider application may be able to present information indicating which patients are located in which examination rooms, waiting rooms, etc.

As described previously, the proximity detection system associated with a hospital, medical office, or other space may also be able to access scheduling information for the hospital, medical office, or other space. In some implementations, the proximity detection system may be able to detect the presence of patients who have arrived for scheduled appointments based on detecting the patients in the hospital, medical office, or other space and determining that the patient has a scheduled appointment near the time when they are detected. The healthcare provider application may be able to provide information to users having the healthcare provider application on their client devices that indicates which patients have arrived for appointments, are late for appointments, have arrived without an appointment, etc. Such information may be presented as notifications provided at the client device hosting the healthcare provider application. For example, a doctor and/or staff associated with a doctor's office may be provided with the notification "John Doe has arrived for their 11:00 AM appointment with Dr. Smith" based on the proximity detection system determining that John Doe has entered the doctor's office and based on determining that John Doe had an 11:00 AM appointment scheduled with Dr. Smith.

In other examples, the healthcare provider application can provide users with other capabilities based on determining that a patient is in a certain location within or has arrived at a hospital, medical office, or other space associated with providing healthcare services. For example, the proximity detection system can determine that a particular patient has arrived at a hospital where a doctor's office is located. While the patient may not have a scheduled appointment with the doctor associated with the doctor's office, the proximity detection system may determine that the patient is due for a check-up within the next month, and that there is an opening in the doctor's schedule at a time near when the patient is detected in the hospital. Based on this determination, the proximity detection system may provide the healthcare provider and/or the patient with information indicating that the patient is due for a check-up and that there is an opening in the schedule of the doctor. A user of the healthcare provider application may be able to contact the patient to ask if they would like to see the doctor during the available time to have their check-up done while they are at the hospital. In other implementations, the proximity detection system may present information to the patient indicating that they are due for a check-up and that the doctor is available, and suggesting or enabling the patient to contact the doctor's office in an attempt to see the doctor for their check-up.

In still other implementations, the healthcare provider application can provide information indicating which users of the healthcare provider application are with a particular patient at a given time. For example, the proximity detection system can determine the locations of a doctor's patients at a particular time, and can further determine the locations of one or more users of a healthcare provider application (e.g., one or more other doctors, nurses, staff members, technicians, specialists, etc.). The healthcare provider application may provide information indicating which patients are which of the other users, for example, by presenting a list of which patients are in which rooms of a doctor's office and which other users are in each of those rooms, by presenting a map showing the locations of both the patients and the other users, etc. In some implementations, the proximity detection system can document which of the other users a particular patient is with at certain times, for example, in a log of the patient's visits. Such a log may be used to track which individuals a patient received treatment from on a particular day or at a particular time, to track which procedures or treatment a patient received on a particular day or at a particular time, to track where the patient traveled within a hospital, doctor's office, or other space, etc.

In some implementations, a healthcare provider application can provide a user with information relating to the status of a patient. Such information can be accessible to the user within the healthcare provider application, or can be presented to the user as a notification, for example, a popup notification presented at their client device. Information relating to a patient's status may include whether the patient has arrived for a scheduled appointment, where the patient is currently waiting, if the patient is currently being seen by another user (e.g., another doctor), if the patient is currently waiting for something or someone, a patient's current medical status (e.g., their current heart rate, blood pressure, respiration rate, body temperature, etc.), or other status information for the patient. For example, a doctor may be provided with a notification when a patient with a scheduled appointment has arrived for their appointment, and may be provided with another notification when the patient is ready to be seen by the doctor (e.g., when the patient is in an examination room). The doctor may also be presented with information indicating when a patient has finished a certain procedure and is ready to be seen by the doctor. For example, a radiologist may indicate that a patient has had x-rays taken and is now free to be seen by the doctor, and can perform operations using a healthcare provider application to indicate that the patient is free. The doctor can then be presented with information indicating that the patient is free to be seen by the doctor. In some implementations, the proximity detection system may have access to a user's medical status information, such as a current heart rate, blood pressure, etc., and may be able to provide notifications based on the information. For example, a doctor using a healthcare provider application may be presented with a notification if a patient's blood pressure reaches a dangerous level.

In still other implementations, a healthcare provider application may be able to present other information associated with a patient to a user of the healthcare provider application. For example, the proximity detection system may be able to determine the location of a doctor as well as the locations of one or more patients of the doctor. As the doctor is approaching an area where the patient is located, for example, when the doctor is within fifty feet of the patient or is near a room where the patient is located, the doctor may be presented and/or be able to access information about the patient. Such information may include the patient's personal information, medical history information, medical status information, etc. By enabling the doctor to review information about the patient before or while the doctor is seeing the patient, the doctor can be better prepared and/or more efficiently interact with the patient. For example, the doctor may be better able to help the patient based on knowing the patient's symptoms, medication allergies, etc., before seeing the patient. The use of the healthcare provider application can additionally reduce or eliminate the need for paper forms and records in a hospital, medical office, or other space associated with providing healthcare services.

In some implementations, a healthcare provider application associated with a user can provide the user with notifications when emergencies occur. For example, the proximity detection system can determine where users of the healthcare provider application are in reference to patients and/or other users of the healthcare provider application. Based on a patient or other user of the healthcare provider application requesting aid, or based on the proximity detection system determining that the patient or other user requires aid (e.g., based on a patient's blood pressure reaching a dangerous level), the proximity detection system may locate other users of the healthcare provider application near the location where aid was requested or is needed, and can notify those users that they are needed and information indicating where they are in reference to where they are needed (e.g., directions from their current location to the patient's room). In some implementations, the proximity detection system may locate users of the healthcare provider application that have certain characteristics. For example, the proximity detection system may only notify doctors and nurses of an emergency relating to a patient, or may only notify doctors and nurses that have a particular expertise (e.g., only doctors and nurses with intensive care unit experience). Additionally, in some instances, a user of a healthcare provider application may be provided with information if a patient is not located in the proper location. For example, a nurse may be provided with a notification if a patient is determined as being in the wrong examination room, if the patient is located in a cardiology department when they should be located in a radiology department, etc.

In some implementations, the proximity detection system may be able to aggregate data relating to one or more patients and/or other users of the proximity detection system, and can perform analysis on the aggregated data. The results of this analysis may be presented as analytics to users of a healthcare provider application and/or a patient application. For example, analytics may monitor the location and/or movement of patients throughout a hospital, medical office, or other space associated with providing healthcare services. Such information may show areas that are the most crowded in the space, areas with the greatest foot traffic, areas of congestion in the space, patterns of movement of patients in the space, etc. In some instances, such data may be presented at an application associated with the proximity detection system using a map format (e.g., showing the density of patients and/or other users in the space) or may be presented in other formats (e.g., as a chart showing the number of patients and/or other users in each region of the space). In some implementations, patient flow-through may be tracked by the proximity detection system, for example, by tracking the amount of time patients spend at a hospital for certain procedures, how far patients travel through the hospital, where patients tend to park or enter the hospital, how much time doctors or others tend to spend with each patient, how much time patients spend waiting to be helped, etc. Such information may be logged and presented to allow optimization of the hospital flow-through, protocols, layout, etc. In some implementations, the logged data can be linked to certain patients, doctors, or other users of the proximity detection system. For example, the average wait time to see certain doctors or to have certain procedures completed can be documented by doctor and/or by procedure. Similarly, a doctor may be able to view information indicating that certain patients typically require more time with the doctor than other patients so that the doctor can appropriately plan their schedule. Other information can be determined and presented based on the aggregation of location data by the proximity detection system. For example, the proximity detection system may be able to suggest that patients use a particular radiology department in a hospital based on determining that other radiology departments in the hospital are more crowded or that a wait time for the particular radiology department is less than for other radiology departments in the hospital. Similarly, users of a healthcare provider application or patient application may be provided with information indicating how busy an eating area is at a current time, which restrooms are currently vacant near the staff, or other information based on the aggregation of location information across multiple users.

Similar functionalities as described above may also be applied to an office building or other work environment setting. For example, employees of a business may be able to host an employee application on their client devices, while managers or other administrators may be able to host a management application on their client devices. The employee and management applications can provide various information or services to business employees, managers, and other administrators using the proximity detection system.

An employee application may be capable of providing various location-based services offered by a proximity detection system. For example, based on the proximity detection system determining an employee's location (e.g., using the trilateration method discussed with respect to FIG. 1), the proximity detection system may determine to provide the employee with certain information, capabilities, notifications, documents, or other information or services. For example, based on determining that an employee is located within a copy room of an office building, the proximity detection system may determine to provide information to the employee that informs the employee how to operate a copy machine located in the copy room. Similarly, based on determining that the employee is located near a secure area within the office building, such as a conference room, store room, or other secured area within the office building, the proximity detection system may perform operations or enable the employee's client device to perform operations to access the secure area. For example, the proximity detection system may automatically unlock a door to a secure area based on determining that the employee's client device is located near the secure area, may cause a credential that enables the employee to access the secure area at a display of the employee's client device, or may otherwise perform operations or provide information to the employee's client device that enables the employee to access the secured area of the office building.

In other examples, an employee may only be provided with certain capabilities or information based on a particular path of movement of the employee's client device determined by the proximity detection system satisfying a required pattern of movement. For example, an employee may only be able to log in to a computer system in their office if the proximity detection system determines that the employee's path of movement has satisfied a predetermined pattern of movement, e.g., by passing by certain wireless sensor beacons in a certain order before attempting to log in to the computer system. Other location-based services may be provided to the employee by the proximity detection system, for example, by enabling the employee to locate other employees or administrators within the office building using the techniques of FIG. 7.

Figure 11:
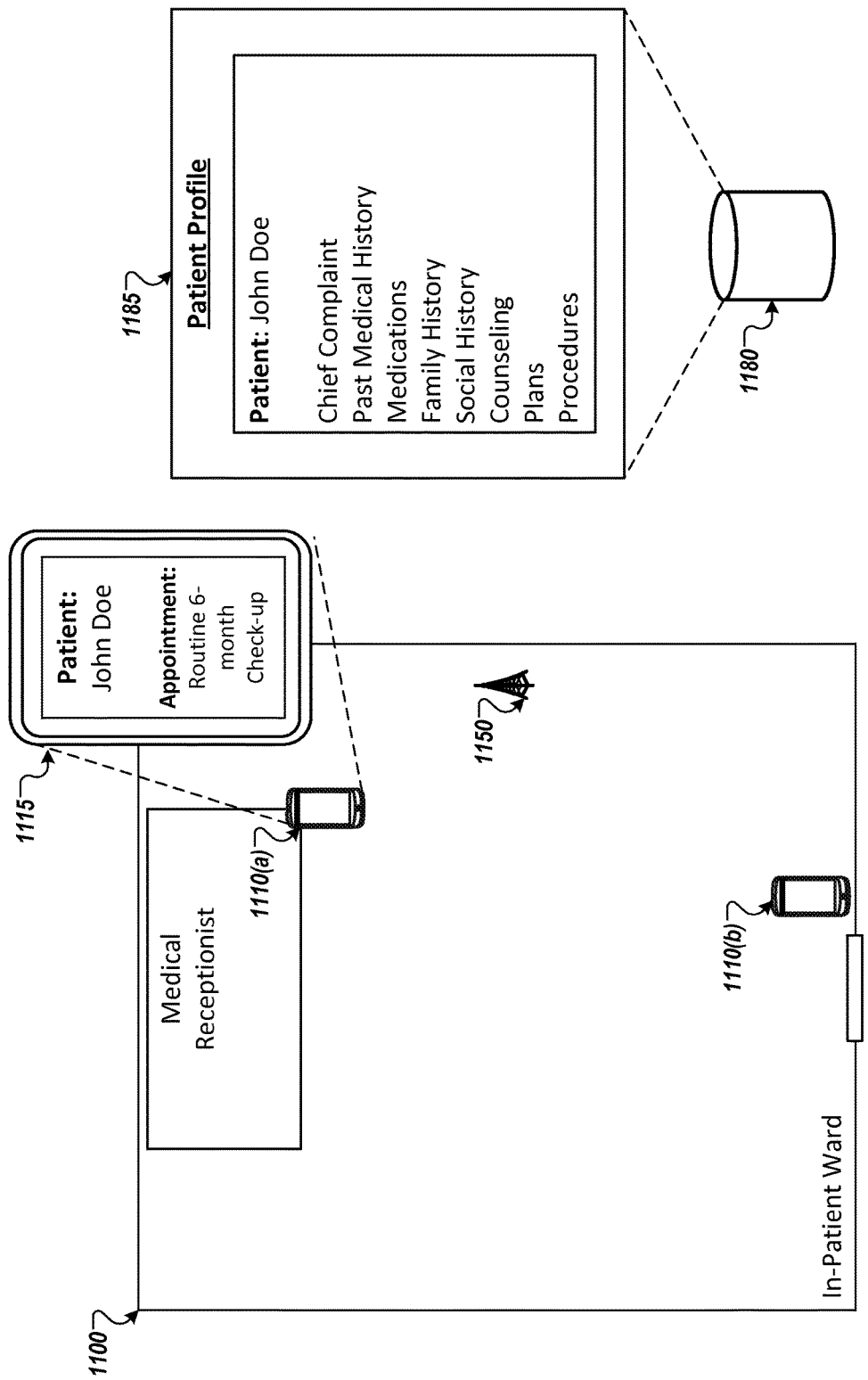
FIGS. 11-12 depict example implementations for providing location-based healthcare information or services using proximity detection technology.

FIG. 11 illustrates another example system for providing location-based healthcare services and content to patients and healthcare providers associated with client devices 1110(*a*)-1110(*b*). As represented in FIG. 11, in some implementations, the healthcare proximity detection system 100 may be used to admit incoming patients within a healthcare facility 1100. In such implementations, the healthcare proximity detection system 100 may include a database 1180 that stores a patient medical 1185.

For example, the healthcare facility 1100 may include a wireless sensor beacon 1150 that is placed within an in-patient ward where patients initially enter to request medical services from healthcare providers associated with the healthcare facility 1100. The in-patient ward of the healthcare facility 1100 may include a medical receptionist associated with the client device 1110(*a*), who welcomes incoming patients that are associated with the client device 1110(*b*) and processes medical information required to register the patients for admission into the healthcare facility 1100. As represented in FIG. 11, the wireless sensor beacon 1150 may initially be detected by the client device 1110(*b*) associated with a patient to be admitted is within proximity and in response, determine that there may be a new patient waiting to be admitted within the in-patient ward. In response, the healthcare proximity detection system 100 may identify the patient associated with the client device 1110(*b*) by receiving identifying information from the client device 1110(*b*) that allows the healthcare proximity detection system 100 to extract the patient profile 1185 corresponding to the patient to be admitted from the database 1180.

The patient profile 1185 may include basic patient information such as chief complain, past medical history, medications, family history, social history, counseling, plans, procedures, or other medical information that may assist a healthcare provider such as a nurse or a physician to provide medical services to the patient associated with the client device 1110(*b*). The wireless sensor beacon 1150 may also be used by the healthcare proximity detection system to transmit the identified patient profile 1185 to the client device 1110(*a*) that may be associated with a healthcare provider such as a medical receptionist, medical secretary, a physician assistant, or any other healthcare provider that enters patient information into the medical records system of the healthcare facility 1100. As represented in FIG. 11, the wireless sensor beacon 1150 may transmit the information from the patient profile 1185 to display on the interface 1115 of the client device 1110(*a*). In the example shown in FIG. 11, the healthcare proximity detection system may associate the patient "John Doe" with the client device 1110(*b*), and in response to the healthcare proximity detection system identifying the patient based on the patient profile 1185, the patient information including the type of appointment, "routine 6-month check-up" may be displayed on the interface 1115 of the client device 1110(*a*) associated with a medical receptionist that processes the patient in the in-patient ward.

Although FIG. 11 represents the identification and transmission of patient information to a client device 1110(*a*) associated with a medical receptionist in response to receiving proximity data from the client device 1110(*b*) associated with the patient, in some implementations, the healthcare proximity system 100 may be used to triage multiple patients that arrive at the in-patient ward of an emergency room within a particular time period. For example, in such implementations, the patient profile 1185 may include information related to an injury severity such as, for example, current patient condition, risk of prolonged physical injury, procedures required, and/or probability of fatality, that may be used to admit patients into the healthcare facility 1200 based on the severity of injuries suffered by each particular patient in relation to injuries suffered by other patients requesting medical services within the in-patient ward of the emergency room. For example, if one patient enters the in-patient ward with a minor bruise, but a second patient enters with a heart attack, the respective patient profiles 1185 for each patient may indicate that the patient with the heart attack may require emergency medical services, and in response, the interface 1115 may display information for the patient with the heart attack and an alert including specific information related to the patient's condition.

In other implementations, the healthcare proximity system 100 in FIG. 11 may be used be used to determine patient room availabilities for patients to be admitted to the healthcare facility 1100. For example, in such implementations, each of the patient rooms may include an individual wireless sensor beacon 1150 that receives proximity data from client devices associated with the admitted patients. In response to receiving proximity data from a nearby client device, the particular wireless sensor beacon 1150 within a particular patient room may transmit a signal to the client device 1110(*a*) associated with a healthcare provider such as a medical receptionist indicating that the particular patient room is occupied. In some instances, the database 1180 of the healthcare proximity system 100 may also include a room occupancy list that displays all occupied and unoccupied rooms based on data transmitted from the individual wireless sensor beacons 1150 located in the particular patient rooms.

In some implementations, the healthcare proximity detection system 100 of FIG. 11 may be used to aggregate data from various patients that are admitted through the in-patient ward of the healthcare facility 1100. For example, the wireless sensor beacon 1150 within the in-patient ward may receive data related to patient visitation from client devices 1110(*b*) associated with various patients such as, for example, average wait time to see a healthcare provider, types of appointments within particular days of the week, volume of appointments within particular time periods of the day, and frequency of particular types of appointments. In such implementations, the healthcare proximity system may aggregate data from the patient profiles of patients associated with the client devices 1110(*b*) and detected by the wireless sensor beacon 1150 within the in-patient ward.

Figure 12:
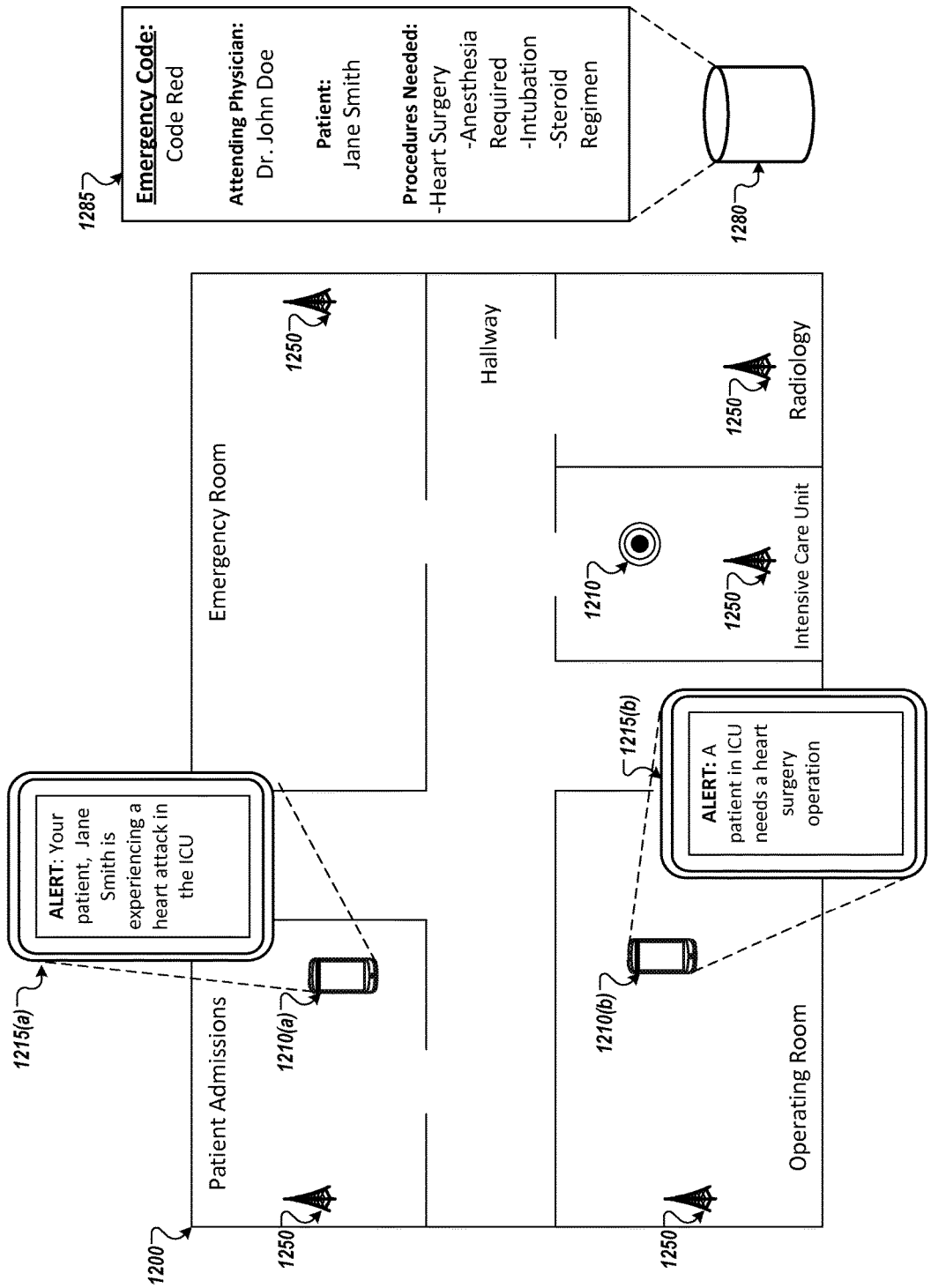

FIG. 12 illustrates another example system for providing location-based educational services and content to patients and healthcare providers associated with client devices 1210(*a*)-1210(*b*). As represented in the example in FIG. 12, in some implementations, the healthcare proximity detection system 100 may be used provide notifications and alerts to healthcare providers in response to a patient requiring emergency medical services. In such implementations, the healthcare proximity detection system 100 within a healthcare facility 1200 may include a database 1280 that stores emergency information 1285 that identifies an emergency code, an attending physician, a patient that needs emergency assistance, and procedures that the patient may need.

For example, the healthcare facility 1200 may include wireless sensor beacons 1250 placed within particular locations of the healthcare facility 1200 such as patient admissions, emergency room, operation room, intensive care unit, and/or radiology. The wireless sensor beacons 1250 may exchange information with the client devices 1210(*a*)-1210(*b*) in response to a medical emergency 1210. For instance, in the example in FIG. 12, a patient "Jane Smith" in the intensive care unit may be having a heart attack, and in response, an attending healthcare provider such as a nurse may transmit the emergency information 1285 to the wireless sensor beacon 1250 in the intensive care unit requesting assistance from nearby healthcare providers associated with client devices 1210(*a*)-1210(*b*). As shown, the emergency information 1285 may include an emergency code such as "Code Red," which indicates that a patient is suffering a cardiopulmonary arrest, an attending physician, "Dr. John Doe," which may be the bedside physician overseeing the wellbeing of the patient "Jane Smith," and procedures needed to resolve the medical emergency 1210 such as "heart surgery." In response, the wireless sensor beacon 1250 within the intensive care unit may be used by the healthcare proximity detection system to transmit notifications including data from the emergency information 1285 to nearby healthcare providers associated with the client devices 1210(*a*)-1210(*b*). In one example, the healthcare provider associated with the client device 1210(*a*) may be the attending physician, "Dr. John Doe," who receives a notification that his patient is coding and a location as shown on an interface 1215(*a*) of the client device 1210(*a*). In another example, an alert may also be sent to healthcare providers in other parts of the hospital that may be notified to conduct an emergency procedure. For instance, a healthcare provider in the operating room that is associated with the client device 1210(*b*) may receive a notification on the interface 1215(*b*) indicating that a patient may need to be prepared for surgical operation. In such an instance, the healthcare provider associated with the client device 1210(*b*) may receive the notification on the interface 1215(*b*) prior to the transfer of the patient "Jane Smith" from the intensive care unit to the operating room.

In some implementations, the healthcare proximity detection system 100 of FIG. 12 may be used to provide alerts and notifications in response to other types of emergency events within the healthcare facility 1200. For example, the medical emergency 1210 may also include other types of emergencies within a healthcare facility such as evacuations, quarantines, or other types of health-related emergencies. In such implementations, the particular wireless beacons 1250 in each of the particular locations in the healthcare facility 1200 may be used to relay location-based alarms or notifications on the interfaces 1215(*a*)-1215(*b*) of the client devices 1210(*a*)-1210(*b*), respectively. For example, in response to a medical emergency 1210 requiring an immediate quarantine, the individual wireless sensor beacons 1250 may be used by the healthcare proximity detection system to transmit location-based instructions to the particular client devices 1210(*a*)-1210(*b*). For instance, the client device 1210(*a*) may receive an instruction to close all exits to the healthcare facility 1200 to prevent any patients from entering the patient admissions department, whereas the client device 1210(*b*) may receive instructions to proceed with sterilization procedures to prevent contamination of the operating room. In such instances, the particular instruction received by each client device may vary based on the location of each individual wireless sensor beacon 1250 in the particular region within the healthcare facility 1200.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

A number of implementations have been described. Nevertheless, it will be understood that various modifications may be made without departing from the spirit and scope of the disclosure. Accordingly, other implementations are within the scope of the following claims.

What is claimed is:

1. A computer-implemented method comprising:
    receiving, from an application instance operating on a first client device, information indicating (i) a patient identifier corresponding to a patient associated with the first client device, (ii) a beacon identifier associated with a wireless proximity beacon that is associated with a physical location within a healthcare facility, and (iii) a proximity of the first client device to the wireless proximity beacon associated with the beacon identifier;
    estimating a physical location of the first client device within the healthcare facility based at least on (i) the beacon identifier associated with the wireless proximity beacon, and (ii) the proximity of the first client device to the wireless proximity beacon;
    accessing a patient profile associated with the patient identifier, the patient profile comprising patient information corresponding to the patient;
    receiving, from each of one or more application instances that operate on one or more respective second client devices associated with one or more healthcare providers of the healthcare facility, (i) a beacon identifier associated with a wireless proximity beacon that is associated with a physical location within a healthcare facility, and (ii) a proximity of the second client device associated with the healthcare provider to the wireless proximity beacon associated with the beacon identifier;
    estimating, for each of the one or more second client devices associated with the one or more healthcare providers, a physical location of the second client device associated with the healthcare provider within the healthcare facility based at least on (i) the beacon identifier associated with the wireless proximity beacon, and (ii) the proximity of the second client device associated with the healthcare provider to the wireless proximity beacon associated with the beacon identifier;
    selecting, from among the one or more second client devices associated with the one or more healthcare providers, a particular second client device associated with a particular healthcare provider based at least on the estimated physical location of the first client device and the estimated physical locations of the one or more second client devices associated with the one or more healthcare providers; and transmitting, to the particular second client device associated with the particular healthcare provider, at least a portion of the patient information for display at an interface of the particular second client device associated with the particular healthcare provider.

2. The computer-implemented method of claim 1, comprising:

determining, based at least on the estimated physical location of the first client device, that the patient associated with the first client device has entered an in-patient ward within the healthcare facility.

3. The computer-implemented method of claim 1, wherein the patient information indicates (i) a medical history, (ii) an appointment associated with a medical consultant, and (iii) a list of symptoms experienced by the patient associated with the first client device.

4. The computer-implemented method of claim 3, wherein selecting the particular second client device associated with the particular healthcare provider comprises selecting, from among the one or more second client devices associated with the one or more healthcare providers, a particular client device associated with the medical consultant; and wherein transmitting at least the portion of the patient information for display at the interface of the particular second client device associated with the particular healthcare provider comprises transmitting, to the particular client device associated with the medical consultant, at least the portion of the patient information for display at an interface of the particular client device associated with the medical consultant.

5. The computer-implemented method of claim 4, wherein transmitting at least the portion of the patient information to the particular client device associated with the medical consultant comprises transmitting, to the particular client device associated with the medical consultant, (i) the medical history, and (ii) the list of symptoms experienced by the patient associated with the first client device for display at the interface of the particular client device associated with the medical consultant.

6. The computer-implemented method of claim 3, comprising:

determining, based at least on the list of symptoms experienced by the patient associated with the first client device, a triage assigned to the patient associated with the first client device; and transmitting, to the particular second client device associated with the particular healthcare provider, information related to the triage assigned to the patient associated with the first client device.

7. The computer-implemented method of claim 6, wherein transmitting the information related to the triage assigned to the patient associated with the first client device comprises transmitting (i) the medical history, and (ii) the list of symptoms experienced by the patient associated with the first client device for display at the interface of the particular second client device associated with the particular healthcare provider.

8. The computer-implemented method of claim 1, comprising:

receiving, based on signals from one or more wireless sensor beacons associated with physical locations within one or more patient rooms within the healthcare facility, information indicating an occupancy of the one or more patient rooms within the healthcare facility;

determining, based at least on the information indicating the occupancy of the one or more patient rooms within the healthcare facility, at least one patient room that is not occupied; and transmitting, to the particular second client device associated with the particular healthcare provider, information related to the at least one patient room that is not occupied.

9. The computer-implemented method of claim 8, wherein transmitting the information related to the at least one patient room that is not occupied comprises transmitting, to the particular second client device associated with the particular healthcare provider and in response to determining, based at least on the estimated physical location of the first client device, that the patient associated with the first client device has entered an in-patient ward within the healthcare facility, a list of room numbers indicating the at least one patient room that is not occupied.

10. The computer-implemented method of claim 1, wherein selecting the particular second client device associated with the particular healthcare provider comprises:

determining a proximity of the particular second client device associated with the particular healthcare provider to the first client device based at least on an estimated physical location of the particular second client device associated with the particular healthcare provider and the estimated physical location of the first client device;

determining that the proximity of the particular second client device associated with the particular healthcare provider to the first client device satisfies a threshold proximity; and selecting the particular second client device associated with the particular healthcare provider based at least on determining that the proximity of the particular second client device associated with the particular healthcare provider to the first client device satisfies the threshold proximity.

11. The computer-implemented method of claim 1, wherein the particular second client device associated with the particular healthcare provider is a second client device that is determined to be have an estimated physical location that is proximate to the estimated physical location of the first client device.

12. The computer-implemented method of claim 1, wherein the particular second client device associated with the particular healthcare provider is a second client device that is determined to have an estimated physical location that is proximate to the physical location within the healthcare facility associated with the wireless proximity beacon having the beacon identifier received from the application instance operating on the first client device.

13. The computer-implemented method of claim 1, comprising:

determining that the proximity of the first client device to the wireless proximity beacon satisfies a threshold proximity; and transmitting, to the particular second client device associated with the particular healthcare provider, at least the portion of the patient information for display at the interface of the particular second client device associated with the particular healthcare provider in response to determining that the proximity of the first client device to the wireless proximity beacon satisfies the threshold proximity.

14. A system comprising:
one or more processing elements; and
non-transitory computer-readable storage media storing instructions that, when executed by the one or more processing elements, cause the system to perform operations comprising:
receiving, from an application instance operating on a first client device, information indicating (i) a patient identifier corresponding to a patient associated with the first client device, (ii) a beacon identifier associated with a wireless proximity beacon that is associated with a physical location within a healthcare facility, and (iii) a proximity of the first client device to the wireless proximity beacon associated with the beacon identifier;
estimating a physical location of the first client device within the healthcare facility based at least on (i) the beacon identifier associated with the wireless proximity beacon, and (ii) the proximity of the first client device to the wireless proximity beacon;
accessing a patient profile associated with the patient identifier, the patient profile comprising patient information corresponding to the patient;
receiving, from each of one or more application instances that operate on one or more respective second client devices associated with one or more healthcare providers of the healthcare facility, (i) a beacon identifier associated with a wireless proximity beacon that is associated with a physical location within a healthcare facility, and (ii) a proximity of the second client device associated with the healthcare provider to the wireless proximity beacon associated with the beacon identifier;
estimating, for each of the one or more second client devices associated with the one or more healthcare providers, a physical location of the second client device associated with the healthcare provider within the healthcare facility based at least on (i) the beacon identifier associated with the wireless proximity beacon, and (ii) the proximity of the second client device associated with the healthcare provider to the wireless proximity beacon associated with the beacon identifier;
selecting, from among the one or more second client devices associated with the one or more healthcare providers, a particular second client device associated with a particular healthcare provider based at least on the estimated physical location of the first client device and the estimated physical locations of the one or more second client devices associated with the one or more healthcare providers; and
transmitting, to the particular second client device associated with the particular healthcare provider, at least a portion of the patient information for display at an interface of the particular second client device associated with the particular healthcare provider.

15. The system of claim 14, wherein the operations comprise:
determining, based at least on the estimated physical location of the first client device, that the patient associated with the first client device has entered an in-patient ward within the healthcare facility.

16. The system of claim 14,
wherein the patient information indicates (i) a medical history, (ii) an appointment associated with a medical consultant, and (iii) a list of symptoms experienced by the patient associated with the first client device.

17. The system of claim 16, wherein selecting the particular second client device associated with the particular healthcare provider comprises selecting, from among the one or more second client devices associated with the one or more healthcare providers, a particular client device associated with the medical consultant; and
wherein transmitting at least the portion of the patient information for display at the interface of the particular second client device associated with the particular healthcare provider comprises transmitting, to the particular client device associated with the medical consultant, at least the portion of the patient information for display at an interface of the particular client device associated with the medical consultant.

18. The system of claim 17, wherein transmitting at least the portion of the patient information to the particular client device associated with the medical consultant comprises transmitting, to the particular client device associated with the medical consultant, (i) the medical history, and (ii) the list of symptoms experienced by the patient associated with the first client device for display at the interface of the particular client device associated with the medical consultant.

19. The system of claim 16, wherein the operations comprise:
determining, based at least on the list of symptoms experienced by the patient associated with the first client device, a triage assigned to the patient associated with the first client device; and
transmitting, to the particular second client device associated with the particular healthcare provider, information related to the triage assigned to the patient associated with the first client device.

20. The system of claim 19, wherein transmitting the information related to the triage assigned to the patient associated with the first client device comprises transmitting (i) the medical history, and (ii) the list of symptoms experienced by the patient associated with the first client device for display at the interface of the particular second client device associated with the particular healthcare provider.

21. The system of claim 14, wherein the operations comprise:
receiving, based on signals from one or more wireless sensor beacons associated with physical locations within one or more patient rooms within the healthcare facility, information indicating an occupancy of the one or more patient rooms within the healthcare facility;
determining, based at least on the information indicating the occupancy of the one or more patient rooms within the healthcare facility, at least one patient room that is not occupied; and
transmitting, to the particular second client device associated with the particular healthcare provider, information related to the at least one patient room that is not occupied.

22. At least one non-transitory computer-readable storage medium storing executable instructions that, when executed by at least one processor, cause the at least one processor to perform operations comprising:
receiving, from an application instance operating on a first client device, information indicating (i) a patient identifier corresponding to a patient associated with the first client device, (ii) a beacon identifier associated with a wireless proximity beacon that is associated with a physical location within a healthcare facility, and (iii) a proximity of the first client device to the wireless proximity beacon associated with the beacon identifier;

estimating a physical location of the first client device within the healthcare facility based at least on (i) the beacon identifier associated with the wireless proximity beacon, and (ii) the proximity of the first client device to the wireless proximity beacon;

accessing a patient profile associated with the patient identifier, the patient profile comprising patient information corresponding to the patient;

receiving, from each of one or more application instances that operate on one or more respective second client devices associated with one or more healthcare providers of the healthcare facility, (i) a beacon identifier associated with a wireless proximity beacon that is associated with a physical location within a healthcare facility, and (ii) a proximity of the second client device associated with the healthcare provider to the wireless proximity beacon associated with the beacon identifier;

estimating, for each of the one or more second client devices associated with the one or more healthcare providers, a physical location of the second client device associated with the healthcare provider within the healthcare facility based at least on (i) the beacon identifier associated with the wireless proximity beacon, and (ii) the proximity of the second client device associated with the healthcare provider to the wireless proximity beacon associated with the beacon identifier;

selecting, from among the one or more second client devices associated with the one or more healthcare providers, a particular second client device associated with a particular healthcare provider based at least on the estimated physical location of the first client device and the estimated physical locations of the one or more second client devices associated with the one or more healthcare providers; and transmitting, to the particular second client device associated with the particular healthcare provider, at least a portion of the patient information for display at an interface of the particular second client device associated with the particular healthcare provider.

* * * * *